United States Patent
Hollis et al.

(10) Patent No.: US 10,927,099 B2
(45) Date of Patent: Feb. 23, 2021

(54) UNSYMMETRIC CCC-NHC PINCER METAL COMPLEXES AND METHODS OF USE THEREOF

(71) Applicant: Mississippi State University, Starkville, MS (US)

(72) Inventors: Thedford Keith Hollis, Starkville, MS (US); Charles Edwin Webster, Starkville, MS (US)

(73) Assignee: Mississippi State University, Starkville, MS (US)

( * ) Notice: Subject to any disclaimer, the term of this patent is extended or adjusted under 35 U.S.C. 154(b) by 0 days.

(21) Appl. No.: 16/496,114

(22) PCT Filed: Mar. 21, 2018

(86) PCT No.: PCT/US2018/023659
§ 371 (c)(1),
(2) Date: Sep. 20, 2019

(87) PCT Pub. No.: WO2018/175659
PCT Pub. Date: Sep. 27, 2018

(65) Prior Publication Data
US 2020/0095228 A1   Mar. 26, 2020

Related U.S. Application Data

(60) Provisional application No. 62/474,171, filed on Mar. 21, 2017, provisional application No. 62/538,347, filed on Jul. 28, 2017.

(51) Int. Cl.
| | | |
|---|---|---|
| C07D 403/10 | (2006.01) | |
| C07F 15/00 | (2006.01) | |
| C07F 15/02 | (2006.01) | |

(52) U.S. Cl.
CPC ........ *C07D 403/10* (2013.01); *C07F 15/0086* (2013.01); *C07F 15/02* (2013.01)

(58) Field of Classification Search
None
See application file for complete search history.

(56) References Cited

U.S. PATENT DOCUMENTS

| | | | |
|---|---|---|---|
| 8,067,100 B2 | 11/2011 | Walters et al. | |
| 8,754,232 B2 | 6/2014 | Tsai | |
| 9,029,804 B2* | 5/2015 | Hollis | H01L 51/0083 |
| | | | 250/459.1 |
| 2019/0016741 A1* | 1/2019 | Hollis | C07F 15/0086 |

FOREIGN PATENT DOCUMENTS

WO    WO2011/050003 A1    4/2011

OTHER PUBLICATIONS

Huckaba et al., Synthesis and Characterization of a 1,3-Phenylene-Bridged N-Alkyl Bis(benzimidazole) CCC-NHC Pincer Ligand Precursor: Homobimetallic Silver and Rhodium Complexes and the Catalytic Hydrosilylation of Phenylacetylene, Organometallics, vol. 32, Dec. 31, 2012.

* cited by examiner

*Primary Examiner* — Kamal A Saeed
(74) *Attorney, Agent, or Firm* — Stites & Harbison PLLC; Sean P. Ritchie

(57) ABSTRACT

Provided herein are unsymmetrical bis(azolium) salts, unsymmetrical CCC-NHC metal complexes, and methods of forming the same. The unsymmetrical bis(azolium) salts include a central aryl ring that is substituted with two heterocyclic rings in an ortho, meta, or para fashion. The unsymmetrical CCC-NHC metal complexes include metalated unsymmetrical bis(azolium) salts. The method of forming the unsymmetrical CCC-NHC metal complexes includes reacting a dihalogenated benzene with a first azole to form a mono(azole)benzene, reacting the mono(azole)benzene with a second azole to form an unsymmetrical bis(azole)benzene, alkylating the unsymmetrical bis(azole)benzene to form an unsymmetrical bis(azolium) salt, and metalating the unsymmetrical bis(azolium) salt to form the unsymmetrical CCC-NHC metal complex. Also provided are a bis-ligated CCC-NHC metal complex and an unsymmetrical bimetallic complex.

8 Claims, 5 Drawing Sheets

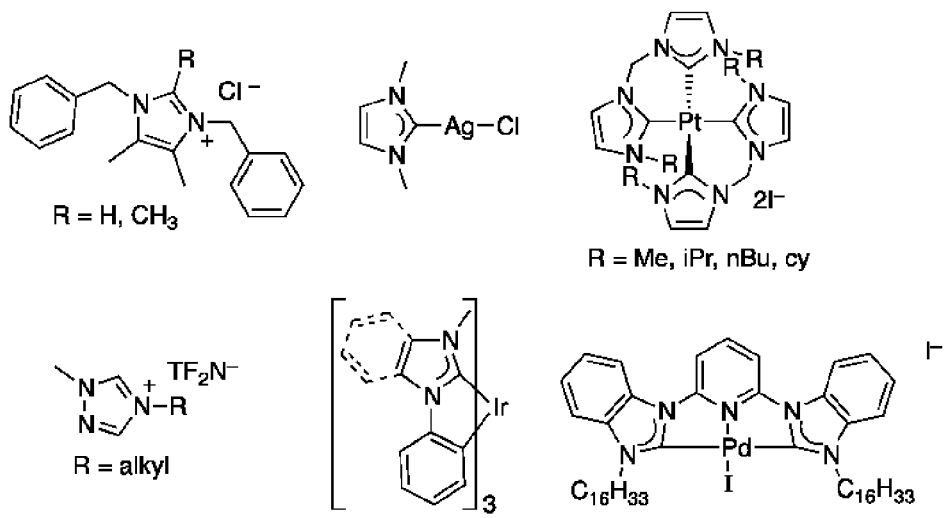
**FIG. 1
(PRIOR ART)**
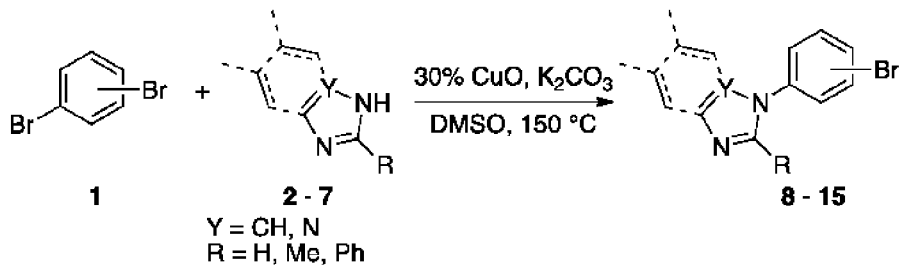
FIG. 2
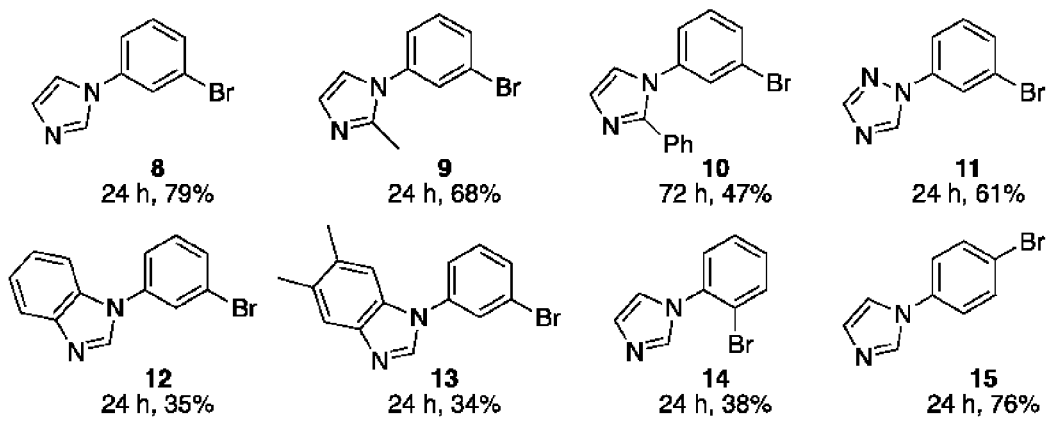
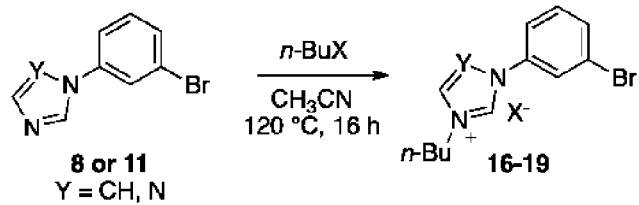

| | het1 | het2 | R | X | | yield |
|---|---|---|---|---|---|---|
| 7 | im | bz | Bu | Cl | 13 | 62% |
| 8 | im | bz | Nx | Cl | 14 | 55% |
| 11 | im | tz | Bu | BPh$_4$ | 15 | 18% |
| 12 | tz | bz | Bu | BPh$_4$ | 16 | 19% |

| | Ar | yield |
|---|---|---|
| 17 | phenyl | 75% |
| 18 | 4-fluorophenyl | 79% |
| 19 | 3,4,5-trifluorophenyl | 68% |
| 20 | 2-naphthyl | 52% |

UNSYMMETRIC CCC-NHC PINCER METAL COMPLEXES AND METHODS OF USE THEREOF

RELATED APPLICATIONS

This application is a national stage application, filed under 35 U.S.C. § 371, of International Patent Application No. PCT/US2018/023659, filed Mar. 21, 2018, which claims priority from U.S. Provisional Application Ser. No. 62/474,171, filed Mar. 21, 2017, and U.S. Provisional Application Ser. No. 62/538,347, filed Jul. 28, 2017, the entire disclosures of which are incorporated herein by this reference.

GOVERNMENT INTEREST

This invention was made with government support under grant number OIA1539035 awarded by the National Science Foundation and grant number P200A120066 awarded by the Department of Education. The government has certain rights in the invention.

TECHNICAL FIELD

The presently-disclosed subject matter generally relates to unsymmetrical salts, CCC-NHC pincer metal complexes, and methods of making and using the same. More specifically, the presently-disclosed subject matter relates to unsymmetrical bis(azolium) salt, mono- and bis-ligated CCC-NHC pincer metal complexes, and methods of making and using the same.

BACKGROUND

Heterocycles are of immense importance biologically and industrially. The pharmaceutical industry has exploited this characteristic to the point where more than 90% of new drugs contain a heterocycle. Important five-membered nitrogen heterocycles include imidazole, benzimidazole, and triazole (representatives of the azoles) and the corresponding azolium salts. Various azolium salts have found widespread use as ionic liquids and have shown biological activity including antitumor, antibacterial, antimicrobial activities, and interaction with DNA. Some of the azolium or azolylidene complexes that have been used in biological and materials applications are shown in FIG. 1.

Azolium salts have also been used in the design of GalTs inhibitors, anion receptors, OLED materials, and as ligand precursors for transition metal complexes, which commonly feature improved stability, catalytic reactivity, and selectivity. For example, azolium salts may be used in the formation of certain carbenes. Carbenes have a long history as reactive intermediates in organic chemistry, and over the last two decades many stable carbenes have been isolated and characterized, which has provided chemists with new reagents. The most popular and widely applied version of these carbenes, N-heterocyclic carbenes (NHCs), have become common as ligands coordinated to transition metals in the field of organometallic chemistry. Because of their strong σ-donating ability, limited dissociation, and neutral charge, NHCs have exceeded phosphine ligands as a means of generating more durable catalysts. As the synthetic utility of NHCs has developed, research has expanded from the typical imidazolium-derived NHCs to include triazole, abnormal NHC (aNHC) ligands (C4 or C5 bound), acyclic and numerous other examples. Further investigations, experimental and theoretical, have found aNHC ligands to be stronger donors and in some cases their complexes were found to have greater reactivity than their C-2 coordinated equivalents.

Despite these recent NHC advances and the widespread use of pincer ligands due to the ease of varying the lateral donor groups, which provides an effective way to alter the properties of the chelated metal center, the development of pincer ligand complexes featuring NHC moieties has suffered from a lack of synthetic methodologies allowing for new and diverse architectures. For example, in 2012, while attempting to synthesize a normal CCC-NHC pincer complex, Braunstein reported that among a mixture of products a pincer complex was isolated containing one "normally-coordinated" NHC and one "abnormally-coordinated" NHC. However, the previously reported efficient one pot synthesis of 1,3-bis(azole)benzenes employing a CuO-catalyzed aryl amination reaction of 1,3-dibromobenzene followed by alkylation yielding symmetrical bis(azolium) salts provided symmetrical CCC-NHC ligand precursors for the generation of transition metal complexes. Additionally, previously reported synthetic methodologies for the preparation of NHC pincer ligand precursors do not directly allow for the expansion of architectural diversity.

Accordingly, there remains a need for a direct, efficient synthesis of unsymmetrical bis(azolium) salts and unsymmetrical CCC-NHC metal complexes.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments, the presently-disclosed subject matter is directed to an unsymmetrical bis(azolium) salt comprising a compound according to Formula I:

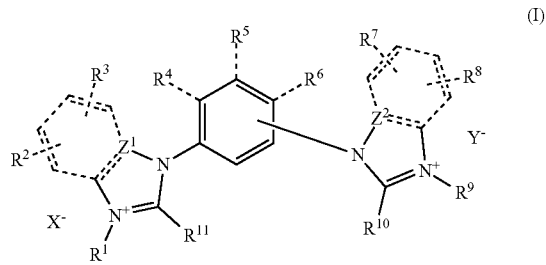

wherein each $R^1$-$R^{11}$ is independently selected from the group consisting of hydrogen, alkyl, aryl, and combinations thereof wherein $Z^1$ and $Z^2$ is each independently selected from the group consisting of CH, $CR^{12}$, N, and combinations thereof wherein X and Y are counteranions; and wherein, when $Z^1$ or $Z^2$ is $CR^{12}$, $R^{12}$ is includes a substituted or unsubstituted C4 alkyl forming a ring structure with the carbon in the Z position and the azole carbon attached thereto.

In some embodiments, the alkyl is a $C_1$-$C_{60}$ alkyl. In one embodiment, the alkyl is selected from the group consisting of branched, ethereal, fluorinated, in-line aryl, and combinations thereof. In another embodiment, the alkyl is selected from the group consisting of methyl, trifluoromethyl, ethyl, propyl, butyl, isopropyl, benzyl, isobutyl, pentyl, hexyl, neohexyl, neopentyl, icosane to hexacontane, and combinations thereof. In some embodiments, the aryl is an unsubstituted aryl. In one embodiment, the aryl is phenyl. In some embodiments, the aryl is a substituted aryl. In one embodiment, the aryl is selected from the group consisting of 4-trimethylmethylaryl, an alkyl substituted aryl, a fluorinated aryl, an ethereal substituted aryl, and combinations thereof.

In some embodiments, $Z^1$ and $Z^2$ are the same and at least one of $R^1$ differs from $R^9$, $R^2$ differs from $R^8$, $R^3$ differs from $R^7$, or $R^{11}$ differs from $R^{10}$. In some embodiment, $Z^1$ and $Z^2$ are different. In one embodiment, one of $Z^1$ and $Z^2$ is CH and one of $Z^1$ and $Z^2$ is $CR^{12}$. In another embodiment, one of $Z^1$ and $Z^2$ is N and one of $Z^1$ and $Z^2$ is CH or $CR^{12}$.

Also provided herein, in some embodiments, is an unsymmetrical CCC-NHC metal complex comprising a mono-ligated metal complex according to Formula III:

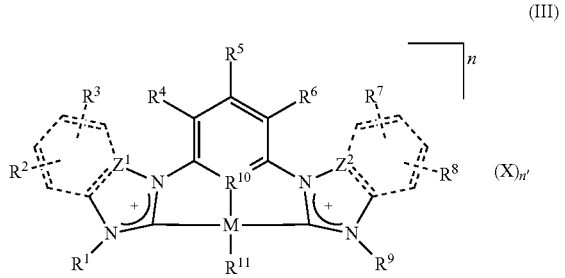

(III)

wherein M is selected from the group consisting of Rh, Ir, Co, Ni, Pd, Pt, Fe, Ru, Os, Mn, V, and Cu; wherein each $R^1$-$R^9$ is independently selected from the group consisting of hydrogen, alkyl, aryl, and combinations thereof wherein $R^{10}$ is C or N; wherein $R^{11}$ is a neutral or charged ligand; wherein $Z^1$ and $Z^2$ are each independently selected from the group consisting of CH, $CR^{12}$, N, and combinations thereof and wherein, when $Z^1$ or $Z^2$ is $CR^{12}$, $R^{12}$ includes a substituted or unsubstituted $C_4$ alkyl forming a ring structure with the carbon in the Z position and the azole carbon attached thereto.

In some embodiments, the alkyl is a $C_1$-$C_{60}$ alkyl. In one embodiment, the alkyl is selected from the group consisting of branched, ethereal, fluorinated, in-line aryl, and combinations thereof. In some embodiments, the aryl is an unsubstituted aryl. In some embodiments, the aryl is a substituted aryl selected from the group consisting of 4-trimethylmethylaryl, an alkyl substituted aryl, a fluorinated aryl, an ethereal substituted aryl, and combinations thereof.

In some embodiments, $Z^1$ and $Z^2$ are the same and at least one of $R^1$ differs from $R^9$, $R^2$ differs from $R^8$, $R^3$ differs from $R^7$, or $R^{11}$ differs from $R^{10}$. In some embodiments, $Z^1$ and $Z^2$ are different.

Further provided herein, in some embodiments, is a method of forming an unsymmetrical CCC-NHC metal complex according to Formula III, the method comprising reacting a dihalogenated benzene with a first azole to form a mono(azole)benzene, reacting the mono(azole)benzene with a second azole to form an unsymmetrical bis(azole) benzene, alkylating the unsymmetrical bis(azole)benzene to form an unsymmetrical bis(azolium) salt, and metalating the unsymmetrical bis(azolium) salt to form the unsymmetrical CCC-NHC metal complex.

Still further provided herein, in some embodiments, is a CCC-NHC metal complex comprising a bis-ligated metal complex according to Formula IV:

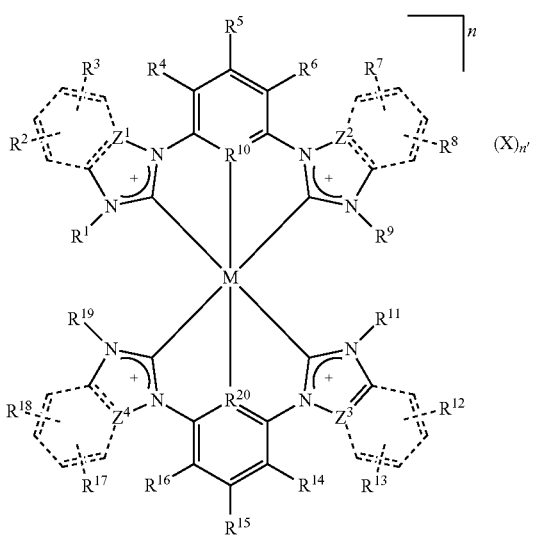

(IV)

wherein M is selected from the group consisting of Rh, Ir, Co, Ni, Pd, Pt, Fe, Ru, Os, Mn, V, and Cu; wherein n is the charge on the complex; wherein each $R^1$-$R^9$ and $R^{11}$-$R^{19}$ is independently selected from the group consisting of hydrogen, alkyl, aryl, and combinations thereof; wherein $R^{10}$ and $R^{20}$ are C or N; wherein X is a counterion and n' is the number of counterions; wherein each $Z^1$-$Z^4$ is independently selected from the group consisting of CH, $CR^{21}$, N, and combinations thereof; and wherein, when $Z^1$, $Z^2$, $Z^3$, or $Z^4$ is $CR^{21}$, $R^{21}$ includes a substituted or unsubstituted $C_4$ alkyl forming a ring structure with the carbon in the Z position and the azole carbon attached thereto.

In some embodiments, M is Pt. In some embodiments, M is Fe. In some embodiments, the complex is unsymmetrical. In some embodiments, the complex is symmetrical. In some embodiments, the alkyl is a $C_1$-$C_{60}$ alkyl. In some embodiments, the alkyl is selected from the group consisting of branched, ethereal, fluorinated, in-line aryl, and combinations thereof. In some embodiments, the aryl is an unsubstituted aryl. In some embodiments, the aryl is a substituted aryl selected from the group consisting of 4-trimethylmethylaryl, an alkyl substituted aryl, a fluorinated aryl, an ethereal substituted aryl, and combinations thereof. In some embodiments, at least one of $Z^1$-$Z^4$ is different at least one other Z. In some embodiments, each of $Z^1$-$Z^4$ is different.

In some embodiments, the complex is selected from the group consisting of bis[2-[1-(N-butylbenzimidazol-2-ylidene)-3-(N-butylimidazol-2-ylidene)phenylene]iron(III) iodide, bis[2-[1-(N-butylbenzimidazol-2-ylidene)-3-(N-butylimidazol-2-ylidene)phenylene]iron(II), and bis[2-[1-(N-butylbenzimidazol-2-ylidene)-3-(N-butyltriazol-2-ylidene)phenylene]iron(III) tetraphenyl borate. In some embodiments, the complex is selected from the group consisting of bis(1,3-bis(N-butyl-imidazol-2'-ylidene)phenylene)iron(III) iodide, bis(1,3-bis(N-methyl-imidazol-2'-ylidene)phenylene)iron(III) iodide, bis(1,3-bis(N-benzylimidazol-2'-ylidene)phenylene)iron(III) bromide, bis (1,3-bis(N-butyl-benzimidazol-2'-ylidene)phenylene)iron (III) iodide, bis(1,3-bis(N-butyl-triazol-2'-ylidene) phenylene)iron(III) iodide, bis(1,3-bis(N-butyl-imidazol-2'-ylidene)phenylene)iron(III) tetraphenylborate, bis(1,3-bis (N-butyl-benzimidazol-2'-ylidene)phenylene)iron(III) tetraphenylborate, bis-[2-(1,3-bis(N-butylimidazol-2-ylidene)phenylene)] iron(II), bis-[2-(1,3-bis(N-benzylimidazol-2-ylidene)phenylene)] iron(II), bis-[2-(1,3-bis(N-butylbenzimidazol-2-ylidene)phenylene)] iron(II), and bis (1,3-bis(N-butyl-benzimidazol-2'-ylidene)5-nitrophenylene)iron(III) hydrogen dinitrate.

Further provided herein, in some embodiments, is a compound comprising an unsymmetrical bimetallic complex according to Formula V:

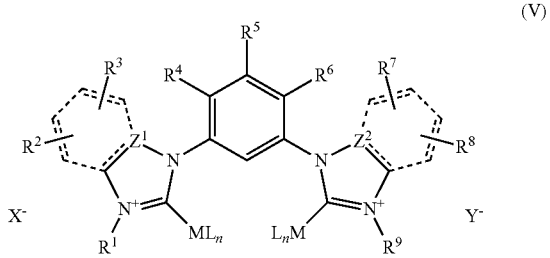

(V)

wherein each $L_n$ is a neutral or anionic ligand; wherein each M is independently selected from the group consisting of Rh, Ir, Co, Ni, Pd, Pt, Fe, Ru, Os, Mn, V, and Cu; wherein each $R^1$-$R^9$ is independently selected from the group consisting of hydrogen, alkyl, aryl, and combinations thereof; wherein X and Y are counterions; wherein $Z^1$ and $Z^2$ are each independently selected from the group consisting of CH, $CR^{10}$, N, and combinations thereof; and wherein, when $Z^1$ or $Z^2$ is $CR^{10}$, $R^{10}$ includes a substituted or unsubstituted $C_4$ alkyl forming a ring structure with the carbon in the Z position and the azole carbon attached thereto.

In some embodiments, at least one M is Pt. In some embodiments, the alkyl is a $C_1$-$C_{60}$ alkyl. In some embodiments, the alkyl is selected from the group consisting of branched, ethereal, fluorinated, in-line aryl, and combinations thereof. In some embodiments, the aryl is an unsubstituted aryl. In some embodiments, the aryl is a substituted aryl selected from the group consisting of 4-trimethylmethylaryl, an alkyl substituted aryl, a fluorinated aryl, an ethereal substituted aryl, and combinations thereof. In some embodiments, $Z^1$ is different from $Z^2$.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 1 shows examples of azolium or azolylidene complexes that are used in biological and materials applications.

FIG. 2 shows a schematic view of the synthesis of mono(azole)benzenes according to an embodiment of the disclosure (Scheme 1).

DESCRIPTION OF EXEMPLARY EMBODIMENTS

Figure 3:
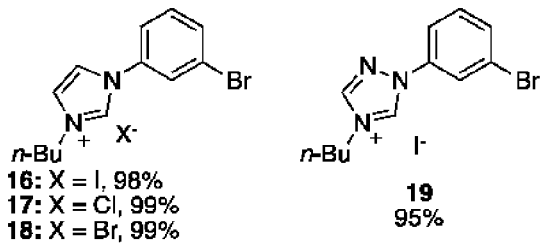
FIG. 3 shows a schematic view of alkylation of select mono(azole)benzenes according to an embodiment of the disclosure.

The details of one or more embodiments of the presently-disclosed subject matter are set forth in this document. However, modifications to embodiments described in this document, and other embodiments, will be evident to those of ordinary skill in the art after a study of the information provided in this document. Additionally, it will be apparent to one of ordinary skill in the art that methods, devices, device elements, materials, procedures and techniques other than those specifically described herein can be applied without resort to undue experimentation. All such modifications, other embodiments, and art-known functional equivalents remain within the spirit and scope of the instant disclosure and are intended to be encompassed by this disclosure. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites, and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

When open-ended terms such as "including" or "including, but not limited to" are used, there may be other non-enumerated members of a list that would be suitable for the making, using or sale of any embodiment thereof.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that whenever a range is disclosed, all subranges and individual values are intended to be encompassed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant. The dashed lines in the various Formulas presented herein represent optional bonds or substituents.

The presently-disclosed subject matter, in some embodiments, includes unsymmetrical salts. In one embodiment, the unsymmetrical salts include unsymmetrical bis(azolium) salts. In another embodiment, the unsymmetrical bis(azolium) salts include a central aryl ring that is substituted with two heterocyclic rings in an ortho, meta, or para fashion. The central aryl linker may be a single arene, such as that derived from benzene, naphthalene, anthracene, pyrene, acenaphthene, or other polycyclic aromatic hydrocarbon, or it may be one or more arenes linked together, such as a biphenyl derivative. The central aryl ring may also have up to three additional substituents attached thereto. Each of the heterocyclic rings contains at least one nitrogen atom, and may include those based on imidazoles, triazoles, CACCs, imidazolines, pyrazoles, and benzimidazoles including normal and abnormal binding modes. In certain embodiments, one or more of the heterocyclic rings may also include other heteroatoms. For example, in some embodiments, the unsymmetrical bis(azolium) salts include compounds according to Formula I:

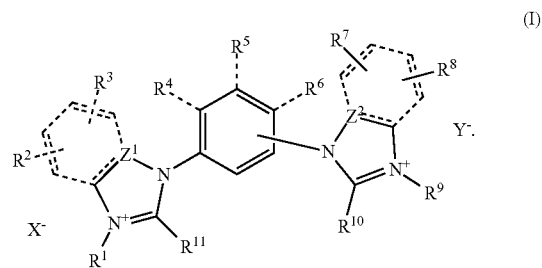

(I)

Each of $R^1$-$R^{11}$ in Formula I independently includes, but is not limited to, hydrogen, alkyl, aryl, or combinations thereof. Suitable alkyl include, but are not limited to, $C_1$ to $C_{60}$ alkyl including branched, ethereal (e.g., PEG-like side chains), fluorinated, and/or in-line aryl such as, but not limited to, methyl, trifluoromethyl, ethyl, propyl, butyl, isopropyl, benzyl, isobutyl, pentyl, hexyl, neohexyl, neopentyl, icosane to hexacontane, or combinations thereof. In one embodiment, the ethereal $C_1$ to $C_{60}$ alkyl including the PEG-like side chains improves and/or increases the solubility of the unsymmetrical bis(azolium) salts as compared to other salts having non-ethereal alkyls. Suitable aryls include, but are not limited to, substituted or unsubstituted aryl such as phenyl, 4-trimethylmethylaryl, aryl groups with 1-5 substituents incorporating alkyl, fluorinated, and/or ethereal substituents, or combinations thereof. Additionally or alternatively, one or more alkyl or aryl substituents of $R^1$-$R^{11}$ in Formula I may contain heteroatoms such as N, O, or S.

Each of $Z^1$ and $Z^2$ in Formula I is associated with a separate heterocyle in the compound, and independently includes, but is not limited to, CH, $CR^{12}$, N, other heteroatoms, or combinations thereof. In one embodiment, when $Z^1$ and/or $Z^2$ is CH, the associated heterocycle is an imidazole derived compound. In another embodiment, when $Z^1$ and/or $Z^2$ is $CR^{12}$, the associated heterocycle is a benzimidazole derived compound. In such embodiments, $R^{12}$ includes a substituted or unsubstituted $C_4$ alkyl forming a ring structure with the carbon in the $Z^1$ or $Z^2$ position and the azole carbon attached thereto. In a further embodiment, when $Z^1$ and/or $Z^2$ is N, the associated heterocycle is a triazole. Suitable triazoles include any heterocycle in the triazole family, such as, but not limited to, 1,2,4-triazole, 1,2,3-triazole, tetrazole, or any other suitable triazole.

The counterions X and Y in Formula I may be the same or different, each independently including any suitable anion. Suitable anions include, but are not limited to, known standard anions and unusual examples such as halides (F, Cl, Br, I), triflate, tetrafluoroborate, hexafluorophosphate, nitrate, hexafluoroantimonate, any of the numerous mono- or di-anionic carboranes (for the dianionic carboranes X and Y are not separate but the same molecule), tetraphenyl borate and variants thereof (e.g., tetraaryl borates with fluorine substitutions ($F_{1-5}$), trifluoromethyl substitutions ($CF_3)_{1-3}$, other alkyl substitutions ($C_1$-$C_{60}$), and/or aryl substitutions ($Ar_{1-3}$)), hydrates thereof, or combinations thereof.

As will be understood by those skilled in the art, there is a difference between at least one atom and/or substituent in the heterocycles of the unsymmetrical bis(azolium) salts disclosed herein. For example, in one embodiment, $Z^1$ is CH and forms heterocycle A, which is an imidazole derived compound, while $Z^2$ is $CR^{12}$ and forms heterocycle B, which is a benzimidazole derived compound, or vice versa. In another example, $Z^1$ is CH or $CR^{12}$ and forms heterocycle A, which is an imidazole or benzimidazole derived compound, respectively, while $Z^2$ is N and forms heterocycle B, which is a triazole derived compound, or vice versa. Additionally or alternatively, one or more of the substituents attached to the heterocycle including $Z^1$ may differ from the corresponding substituent attached to heterocycle including $Z^2$. In Formula I above, the substituents attached to heterocycle A include $R^1$, $R^2$, $R^3$, and $R^{11}$, and the substituents attached to heterocycle B include $R^7$, $R^8$, $R^9$, and $R^{10}$. A difference in corresponding substituents would therefore include, for example, a difference between $R^{11}$ in heterocycle A and $R^{10}$ in heterocycle B. Additionally, it is to be understood that the compounds according to Formula I may include isomers thereof.

By way of example, and not intended to limit the scope of the Formula I, in some embodiments, each of $R^1$ and $R^9$ is independently n-butyl or neohexyl. In some embodiments, $Z^1$ and $Z^2$ are the same. For example, in one embodiment, $Z^1$ and $Z^2$ are both CH. In some embodiments, $R^{10}$ or $R^{11}$ is $CH_3$, $C_6H_5$, or $CH(CH_3)_2$. In some embodiments, $Z^1$ is CH and $Z^2$ is $CR^{12}$ or $Z^1$ is $CR^{12}$ and $Z^2$ is CH. In some embodiments, $Z^1$ is CH and $Z^2$ is N or $Z^1$ is N and $Z^2$ is CH. In some embodiments, $Z^1$ is N and $Z^2$ is $CR^{12}$ or $Z^1$ is $CR^{12}$ and $Z^2$ is N. In some embodiments, $R^2$ and $R^3$ and/or $R^7$ and $R^8$ are $CH_3$. In some embodiments, the heterocycle containing $Z^2$ is in the ortho position. In some embodiments, the heterocycle containing $Z^2$ is in the meta position. In some embodiments, the heterocycle containing $Z^2$ is in the para position and $R^6$ is not present. In some embodiments, $R^4$, $R^5$, and/or $R^6$ are H.

The presently-disclosed subject matter also includes a method of making the unsymmetrical salts described herein. In some embodiments, the method includes first reacting a dihalogenated benzene with a first azole to form a mono (azole)benzene (FIG. 2). The dihalogenated benzene includes any suitable halogen, such as bromide (e.g., any dibromobenzene), iodide, or chloride; and/or any suitable pseudohalide sulfonate, such as triflate (e.g., any bistriflatobenzene) or tosylate. In one embodiment, the dihalogenatedbenzene and the first azole are reacted in the presence of 30% CuO, $K_2CO_3$, and DMSO at an elevated temperature of 150° C. to form the mono(azole)benzene. In certain embodiments, the mono(azole)benzene may be alkylated to form an alkylated mono(azole)benzene (FIG. 3). These mono(azole)benzenes and alkylated mono(azole)benzenes according to Formula II below form stable precursors to the unsymmetrical bis(azolium) salts, where $R^1$-$R^7$, X, and Z are as defined above with respect to Formula I.

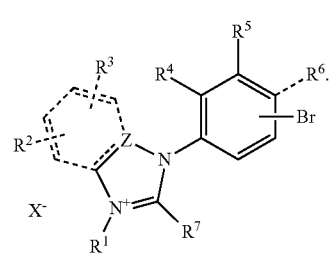

(II)

Figure 6:
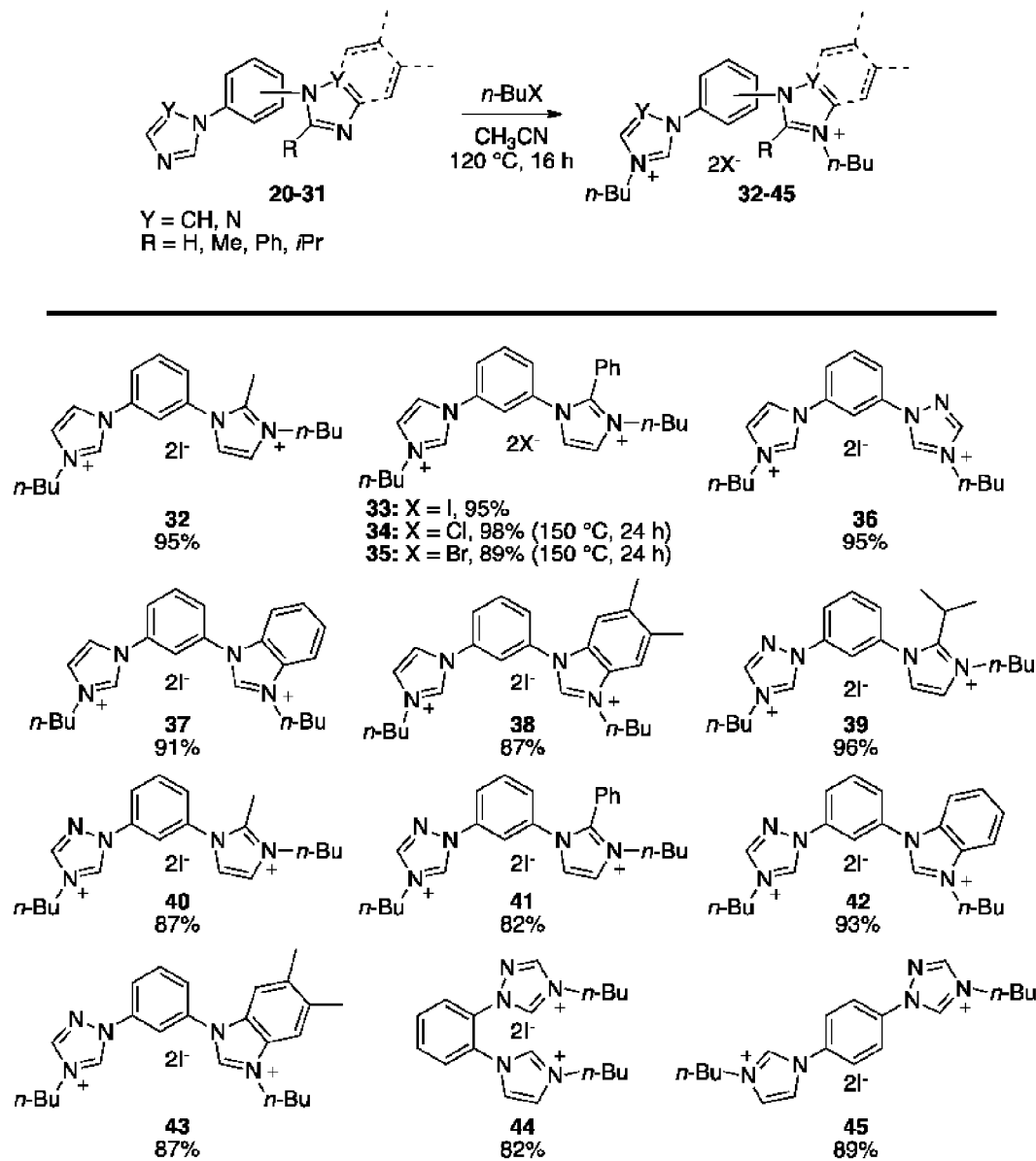
FIG. 6 shows a schematic view of the synthesis of unsymmetrical bis(azolium) salts according to an embodiment of the disclosure.

Following formation of the mono(azole)benzene, the method includes reacting the mono(azole)benzene with a second azole to form an unsymmetrical bis(azole)benzene (FIG. 4), and then alkylating the unsymmetrical bis(azole) benzene to form the unsymmetrical bis(azolium) salts (FIG. 6). The mono(azole)benzene and the second azole may be reacted in the presence of 30% CuO, $K_2CO_3$ and DMSO at an elevated temperature of 150° C. to form the bis(azole) benzene. Additionally or alternatively, the bis(azole)benzene may be alkylated in the presence of n-BuX and $CH_3CN$ at an elevated temperature of 120° C., where X is any suitable anion disclosed here. Although described above with regard to specific reaction conditions, as will be appreciated by those skilled in the art the method is not so limited and may include any suitable solution, catalyst, temperature, or other variation in reaction conditions.

In some embodiments, the methods of making the unsymmetrical salts described herein permit, facilitate, and/or provide expansion of the architectural diversity of compounds featuring unsymmetrical diazoles. The diverse unsymmetrical salt compounds disclosed herein have many different applications, including, but not limited to, pharmacological treatments, bio-active agents, synthesis of pincer complexes, and/or synthesis bimetallic complexes. For example, the unsymmetrical salts disclosed herein may form precursors to CCC-NHC metal complexes and/or bi-metallic complexes.

Accordingly, the presently-disclosed subject matter further includes CCC-NHC metal complexes and methods of making the same. In some embodiments, the CCC-NHC metal complexes include unsymmetrical mono-ligated metal complexes according to Formula III:

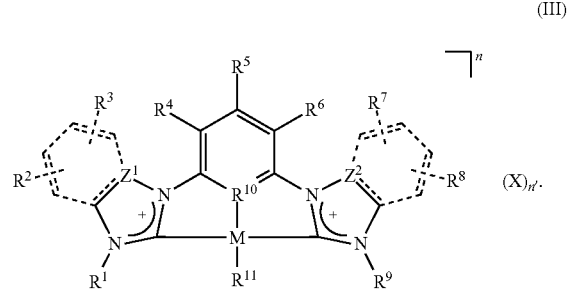

(III)

M in Formula III is any suitable metal for forming a CCC-NHC metal complex. Suitable metals include, but are not limited to, any transition metal, metal, or metalloid. For example, suitable metals may include Rh, Ir, Co, Ni, Pd, Pt, Fe, Ru, Os, Mn, V, or Cu. In some embodiments, the metal is selected from the group consisting of Ni, Pd, Pt, and Rh. In one embodiment, the metal is Pt.

Each of $R^9$ in Formula III independently includes, but is not limited to, hydrogen, alkyl, aryl, or combinations thereof. Suitable alkyl include, but are not limited to, $C_1$ to $C_{60}$ alkyl including branched, ethereal (e.g., PEG-like side chains), fluorinated, and/or in-line aryl such as, but not limited to, methyl, trifluoromethyl, ethyl, propyl, butyl, isopropyl, benzyl, isobutyl, pentyl, hexyl, neohexyl, neopentyl, icosane to hexacontane, or combinations thereof. In one embodiment, the ethereal $C_1$ to $C_{60}$ alkyl including the PEG-like side chains improves and/or increases the solubility of the unsymmetrical bis(azolium) salts as compared to other salts having non-ethereal alkyls. Suitable aryls include, but are not limited to, substituted or unsubstituted aryl such as phenyl, 4-trimethylmethylaryl, aryl groups with 1-5 substituents incorporating alkyl, fluorinated, and/or ethereal substituents, or combinations thereof. Additionally or alternatively, one or more alkyl or aryl substituents of $R^1$-$R^9$ in Formula III may contain heteroatoms such as N, O, or S.

$R^{10}$ is C or N.

$R^{11}$ is any neutral or charged ligand that may be monodentate, bidentate, or tridentate. In some embodiments, $R^{11}$ is Cl. In some embodiments, $R^{11}$ is OAr. In some embodiments, where $R^{11}$ is OAr, Ar is phenyl, 4-fluorophenyl, 3,4,5-trifluorophenyl, or 2-naphthyl.

Each of $Z^1$ and $Z^2$ in Formula III is associated with a separate heterocyle in the compound, and independently includes, but is not limited to, CH, $CR^{12}$, N, other heteroatoms, or combinations thereof. In one embodiment, when $Z^1$ and/or $Z^2$ is CH, the associated heterocycle is an imidazole derived compound. In another embodiment, when $Z^1$ and/or $Z^2$ is $CR^{12}$, the associated heterocycle is a benzimidazole derived compound. In such embodiments, $R^{12}$ includes a substituted or unsubstituted $C_4$ alkyl forming a ring structure with the carbon in the $Z^1$ or $Z^2$ position and the azole carbon attached thereto. In a further embodiment, when $Z^1$ and/or $Z^2$ is N, the associated heterocycle is a triazole. Suitable triazoles include any heterocycle in the triazole family, such as, but not limited to, 1,2,4-triazole, 1,2,3-triazole, tetrazole, or any other suitable triazole.

The charge on the complex is represented by n, which may be negative or positive and is typically in the range of −2 to +3. In some embodiments, however, n may be outside the −2 to +3 range.

X is a counterion and n' represents the number of counterions necessary to balance the charge n on the complex. Each counterion may be the same or different, each independently including any suitable anion. Suitable anions include, but are not limited to, known standard anions and unusual examples such as halides (F, Cl, Br, I), triflate, tetrafluoroborate, hexafluorophosphate, nitrate, hexafluoroantimonate, any of the numerous mono- or di-anionic carboranes, tetraphenyl borate and variants thereof (e.g., tetraaryl borates with fluorine substitutions ($F_{1-5}$), trifluoromethyl substitutions $(CF_3)_{1-3}$, other alkyl substitutions ($C_1$-$C_{60}$), and/or aryl substitutions ($Ar_{1-3}$)), hydrates thereof, or combinations thereof.

Similar to the unsymmetrical bis(azolium) salts, and as will be understood by those skilled in the art, there is a difference between at least one atom and/or substituent in the heterocycles of the unsymmetrical CCC-NHC metal complexes according to Formula III. For example, in one embodiment, the $Z^1$ and $Z^2$ are different. In another embodiment, one or more of the substituents attached to the heterocycle including $Z^1$ differs from the corresponding substituent attached to the heterocycle including $Z^2$. In a further embodiment, the heterocycles include differences in both $Z^1$ and $Z^2$, as well as at least one substituent attached thereto. Additionally, it is to be understood that the compounds according to Formula III may include isomers thereof.

By way of example, and not intended to limit the scope of the Formula III, in some embodiments, each of $R^1$ and $R^9$ is independently n-butyl or neohexyl. In some embodiments, $Z^1$ and $Z^2$ are the same. In some embodiments, $Z^1$ is CH and $Z^2$ is $CR^{12}$ or $Z^1$ is $CR^{12}$ and $Z^2$ is CH. In some embodiments, $Z^1$ is CH and $Z^2$ is N or $Z^1$ is N and $Z^2$ is CH. In some embodiments, $Z^1$ is N and $Z^2$ is $CR^{12}$ or $Z^1$ is $CR^{12}$ and $Z^2$ is N. In some embodiments, $R^2$ and $R^3$ and/or $R^7$ and $R^8$ are H. In some embodiments, $R^2$ and $R^3$ and/or $R^7$ and $R^8$ are $CH_3$. In some embodiments, $R^4$, $R^5$, and/or $R^6$ are H.

As noted above, the unsymmetrical CCC-NHC metal complexes may be formed from the unsymmetrical bis (azolium) salts. For example, in some embodiments, a method of making unsymmetrical CCC-NHC metal complexes includes combining two bis-salts in an organic solvent and then treating with an initial metalation source. Next, the method includes adding a transmetalating agent, followed by quenching the reaction and isolation of the complex. In one embodiment, the initial metalation source is zirconium tetrakisdimethyl amido ($Zr(NMe_2)_4$). The initial metalation source may be added in any suitable amount depending upon the reagents and reaction conditions. Suitable amounts of the initial metalation source include, but are not limited to, between 1 and 2.5 equivalents. In another embodiment, the transmetalating agent is [$PtCl_2(COD)$]. Similar to the initial metalation source, the transmetalating agent may be added in any suitable amount depending upon the reagents and reaction conditions. Suitable amounts of the transmetalating agent include, but are not limited to, about 1 equivalent. In certain embodiments, the CCC-NHC complexes may be reacted with various NaOAr salts in order to form M-OAr complexes, such as Pt—OAr.

In some embodiments, the CCC-NHC metal complexes include bis-ligated metal complexes according to Formula IV:

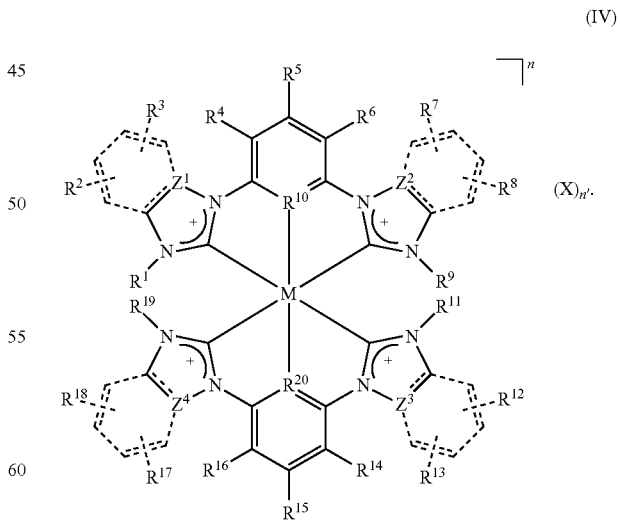

(IV)

M in Formula IV is any suitable metal for forming a CCC-NHC metal complex. Suitable metals include, but are not limited to, any transition metal, metal, or metalloid. For example, suitable metals may include Rh, Ir, Co, Ni, Pd, Pt, Fe, Ru, Os, Mn, V, or Cu. In some embodiments, the metal is selected from the group consisting of Ni, Pd, Pt, and Rh. In one embodiment, the metal is Pt. In one embodiment, the metal is Os. In one embodiment, the metal is Ir. In one embodiment, the metal is Fe.

Each of $R^1$-$R^9$ and $R^{11}$-$R^{19}$ in Formula IV independently includes, but is not limited to, hydrogen, alkyl, aryl, or combinations thereof. Suitable alkyl include, but are not limited to, $C_1$ to $C_{60}$ alkyl including branched, ethereal (e.g., PEG-like side chains), fluorinated, and/or in-line aryl such as, but not limited to, methyl, trifluoromethyl, ethyl, propyl, butyl, isopropyl, benzyl, isobutyl, pentyl, hexyl, neohexyl, neopentyl, icosane to hexacontane, or combinations thereof. In one embodiment, the ethereal $C_1$ to $C_{60}$ alkyl including the PEG-like side chains improves and/or increases the solubility of the unsymmetrical bis(azolium) salts as compared to other salts having non-ethereal alkyls. Suitable aryls include, but are not limited to, substituted or unsubstituted aryl such as phenyl, 4-trimethylmethylaryl, aryl groups with 1-5 substituents incorporating alkyl, fluorinated, and/or ethereal substituents, or combinations thereof. Additionally or alternatively, one or more alkyl or aryl substituents of $R^1$-$R^9$ and $R^{11}$-$R^{19}$ in Formula IV may contain heteroatoms such as N, O, or S.

$R^{10}$ and $R^{20}$ are C or N, and may be the same or different.

Each of $Z^1$-$Z^4$ in Formula IV is associated with a separate heterocyle in the compound, and independently includes, but is not limited to, CH, $CR^{21}$, N, other heteroatoms, or combinations thereof. In one embodiment, when $Z^1$, $Z^2$, $Z^3$, and/or $Z^4$ is CH, the associated heterocycle is an imidazole derived compound. In another embodiment, when $Z^1$, $Z^2$, $Z^3$, and/or $Z^4$ is $CR^{21}$, the associated heterocycle is a benzimidazole derived compound. In such embodiments, $R^{21}$ includes a substituted or unsubstituted $C_4$ alkyl forming a ring structure with the carbon in the $Z^1$, $Z^2$, $Z^3$, and/or $Z^4$ position and the azole carbon attached thereto. In a further embodiment, when $Z^1$, $Z^2$, $Z^3$, and/or $Z^4$ is N, the associated heterocycle is a triazole. Suitable triazoles include any heterocycle in the triazole family, such as, but not limited to, 1,2,4-triazole, 1,2,3-triazole, tetrazole, or any other suitable triazole.

The charge on the complex is represented by n, which may be negative or positive and is typically in the range of −2 to +3. In some embodiments, however, n may be outside the −2 to +3 range.

X is a counterion and n' represents the number of counterions necessary to balance the charge n on the complex. Each counterion may be the same or different, each independently including any suitable anion. Suitable anions include, but are not limited to, known standard anions and unusual examples such as halides (F, Cl, Br, I), triflate, tetrafluoroborate, hexafluorophosphate, nitrate, hexafluoroantimonate, any of the numerous mono- or di-anionic carboranes, tetraphenyl borate and variants thereof (e.g., tetraaryl borates with fluorine substitutions $(F_{1-5})$, trifluoromethyl substitutions $(CF_3)_{1-3}$, other alkyl substitutions $(C_1$-$C_{60})$, and/or aryl substitutions $(Ar_{1-3}))$, hydrates thereof, or combinations thereof.

In some embodiments, the bis-ligated CCC-NHC metal complexes are symmetrical. In such embodiments, each of $Z^1$, $Z^2$, $Z^3$, and $Z^4$ is the same. Examples of such complexes include, but are not limited to, bis(1,3-bis(N-butyl-imidazol-2'-ylidene)phenylene)iron(III) iodide, bis(1,3-bis(N-methyl-imidazol-2'-ylidene)phenylene)iron(III) iodide, bis(1,3-bis(N-benzylimidazol-2'-ylidene)phenylene)iron(III) bromide, bis(1,3-bis(N-butyl-benzimidazol-2'-ylidene)phenylene) iron(III) iodide, bis(1,3-bis(N-butyl-triazol-2'-ylidene)phenylene)iron(III) iodide, bis(1,3-bis(N-butyl-imidazol-2'-ylidene)phenylene)iron(III) tetraphenylborate, bis(1,3-bis(N-butyl-benzimidazol-2'-ylidene)phenylene)iron(III) tetraphenylborate, bis-[2-(1,3-bis(N-butylimidazol-2-ylidene)phenylene)] iron(II), bis-[2-(1,3-bis(N-benzylimidazol-2-ylidene)phenylene)] iron(II), bis-[2-(1,3-bis(N-butylbenzimidazol-2-ylidene)phenylene)] iron(II), and bis (1,3-bis(N-butyl-benzimidazol-2'-ylidene)5-nitrophenylene)iron(III) hydrogen dinitrate.

Alternatively, in some embodiments, the bis-ligated CCC-NHC metal complexes are unsymmetrical, including a difference in at least one atom and/or substituent between two or more of the heterocycles contained therein. As will be appreciated by those skilled in the art, differences between two or more of the heterocycles includes complexes with one different heterocycle and three identical heterocycles (i.e., one different heterocycle), a first set of identical heterocycles and a second set of identical heterocycles that differs from the first (i.e., two different heterocycles), two identical heterocycles and two different heterocycles each differing from the identical heterocycles and each other (i.e., three different heterocycles), or four different heterocycles. For example, in one embodiment, at least one heterocycle include a different Z from at least one other heterocycle in the complex. In another embodiment, one or more of the substituents attached to one heterocycle differs from the corresponding substituent attached to at least one other heterocycle in the complex. In a further embodiment, at least one of the heterocycles include differences in both Z and at least one substituent attached thereto as compared to at least one other heterocycle. Suitable unsymmetrical bis-ligated CCC-NHC metal complexes include, but are not limited to, bis[2-(N-butylbenzimidazol-2-ylidene)-3-(N-butylimidazol-2-ylidene)phenylene]iron(III) iodide, bis[2-[1-(N-butyl-benzimidazol-2-ylidene)-3-(N-butylimidazol-2-ylidene) phenylene]iron(II), and bis[2-[1-(N-butylbenzimidazol-2-ylidene)-3-(N-butyltriazol-2-ylidene)phenylene]iron(III) tetraphenyl borate.

By way of example, and not intended to limit the scope of the Formula IV, in some embodiments, each of $R^{10}$ and $R^{20}$ is independently C. In some embodiments, one of $R^{10}$ and $R^{20}$ is C and one of $R^{10}$ and $R^{20}$ is N. In some embodiments, $Z^1$, $Z^2$, $Z^3$, and $Z^4$ are the same. In some embodiments, at least one of $Z^1$, $Z^2$, $Z^3$, and $Z^4$ is different from the others. In some embodiments, each of $Z^1$, $Z^2$, $Z^3$, and $Z^4$ is different from the others. In some embodiments, at least one of $Z^1$, $Z^2$, $Z^3$, and $Z^4$ is CH. In some embodiments, at least one of $Z^1$, $Z^2$, $Z^3$, and $Z^4$ is $CR^{21}$. In some embodiments, at least one of $Z^1$, $Z^2$, $Z^3$, and $Z^4$ is N. In some embodiments, $Z^1$ and $Z^3$ are $CR^{21}$ and $Z^2$ and $Z^4$ are CH. In some embodiments, $R^2$ and $R^3$ and/or $R^{12}$ and $R^{13}$ are $CH_3$. In some embodiments, at least one of $R^4$, $R^5$, $R^6$, $R^{14}$, $R^{15}$, and $R^{16}$ is $CH_3$. In some embodiments, each of $R^4$, $R^5$, $R^6$, $R^{14}$, $R^{15}$, and $R^{16}$ is H. In some embodiments, each of $R^1$, $R^9$, $R^{11}$, and $R^{19}$ is independently butyl, methyl, or phenyl.

In some embodiments, a method of making bis-ligated CCC-NHC metal complexes includes combining two bis-salts in an organic solvent and then treating with an initial metalation source. Next, the method includes adding a transmetalating agent, followed by quenching the reaction and isolation of the complex. In one embodiment, the initial metalation source is zirconium tetrakisdimethyl amido (Zr$(NMe_2)_4$). The initial metalation source may be added in any suitable amount depending upon the reagents and reaction conditions. Suitable amounts of the initial metalation source include, but are not limited to, between 1 and 2.5 equivalents. In another embodiment, the transmetalating agent is FeCl₃. Similar to the initial metalation source, the transmetalating agent may be added in any suitable amount depending upon the reagents and reaction conditions. Suitable amounts of the transmetalating agent include, but are not limited to, about 1 equivalent. As will be appreciated by those skilled in the art, the selection of the bis-salts will determine the structure of the resulting bis-ligated CCC-NHC metal complexes. Accordingly, the desired heterocycles in the bis-ligated CCC-NHC metal complexes may be obtained by selecting the corresponding bis-salts.

The CCC-NHC pincer metal complexes disclosed herein may be used in a variety of applications, including, but not limited to, light emission and bio-active agents. In some embodiments, the unsymmetrical CCC-NHC pincer platinum complexes disclosed herein represent a new class of pincer metal complexes that demonstrate photoluminescent emission upon irradiation with UV light. In one embodiment, these complexes form highly efficient emitters of light in various portions of the light spectrum. In another embodiment, light emitting applications include, but are not limited to, photoluminescence (both fluorescence, phosphorescence) and electroluminescence. Existing OLED devices, which are prevalent in flat panel displays that are found in cell phones, flat screen televisions, computer monitors, laptops, etc., have significant limitations in the blue region of the spectrum. In contrast thereto, one or more of the complexes disclosed herein provide highly efficient, air-stable photoluminescence in the blue and other regions of the spectrum. As such, in a further embodiment, the unsymmetrical CCC-NHC pincer metal complexes disclosed herein may be used as modern organic light emitting diodes (OLEDs).

As another example, CCC-NHC pincer metal complexes disclosed herein may be used as a replacement for existing platinum-based chemotherapeutic agents, which have broad applicability in many otherwise nearly untreatable cancers. Additionally, these molecules may be employed as catalysts in a wide variety of organic transformations and reactions related to energy sciences and the pharmaceutical industry. Other applications and uses are well known in the field and would be recognized by a person of skill in the art having access to the disclosed new class of unsymmetrical CCC-NHC pincer metal complexes.

Still further provided herein, in some embodiments, are unsymmetrical bimetallics according to Formula V:

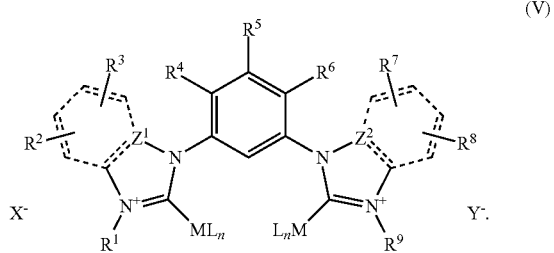

(V)

Each of $R^9$ in Formula V independently includes, but is not limited to, hydrogen, alkyl, aryl, or combinations thereof. Suitable alkyl include, but are not limited to, $C_1$ to $C_{60}$ alkyl including branched, ethereal (e.g., PEG-like side chains), fluorinated, and/or in-line aryl such as, but not limited to, methyl, trifluoromethyl, ethyl, propyl, butyl, isopropyl, benzyl, isobutyl, pentyl, hexyl, neohexyl, neopentyl, icosane to hexacontane, or combinations thereof. In one embodiment, the ethereal $C_1$ to $C_{60}$ alkyl including the PEG-like side chains improves and/or increases the solubility of the unsymmetrical bis(azolium) salts as compared to other salts having non-ethereal alkyls. Suitable aryls include, but are not limited to, substituted or unsubstituted aryl such as phenyl, 4-trimethylmethylaryl, aryl groups with 1-5 substituents incorporating alkyl, fluorinated, and/or ethereal substituents, or combinations thereof. Additionally or alternatively, one or more alkyl or aryl substituents of $R^1$-$R^9$ in Formula V may contain heteroatoms such as N, O, or S.

Each $Z^1$ and $Z^2$ in Formula V independently includes, but is not limited to, CH, $CR^{10}$, N, other heteroatoms, or combinations thereof. In one embodiment, when $Z^1$ and/or $Z^2$ is CH, the associated heterocycle is an imidazole derived compound. In another embodiment, when $Z^1$ and/or $Z^2$ is $CR^{10}$, the associated heterocycle is a benzimidazole derived compound. In such embodiments, $R^{10}$ includes a substituted or unsubstituted $C_4$ alkyl forming a ring structure with the carbon in the $Z^1$ or $Z^2$ position and the azole carbon attached thereto. In a further embodiment, when $Z^1$ and/or $Z^2$ is N, the associated heterocycle is a triazole. Suitable triazoles include any heterocycle in the triazole family, such as, but not limited to, 1,2,4-triazole, 1,2,3-triazole, tetrazole, or any other suitable triazole.

Each M in Formula V independently includes any suitable metal for forming a bimetallic. Suitable metals include, but are not limited to, any transition metal, metal, or metalloid. For example, suitable metals may include Rh, Ir, Co, Ni, Pd, Pt, Fe, Ru, Os, Mn. In some embodiments, the metal is selected from the group consisting of Ni, Pd, Pt, and Rh. In one embodiment, the metal is Pt.

Each $L_n$ in Formula V independently includes any suitable neutral or anionic ligand. Suitable neutral ligands include, but are not limited to, DMSO, acetone, any alkene, norbornene, cyclooctadiene, phosphines, amines, n-heterocyclic carbenes, combinations thereof, or any other suitable combination of neutral ligands that are mono-, bi-, or tri-dentate. Suitable anionic ligands include, but are not limited to, iodide, bromide, chloride, fluoride, triflate, tosylates, nitrate, phosphide, amido, or combinations thereof.

The counterions X and Y in Formula V may be the same or different, each independently including any suitable anion. Suitable anions include, but are not limited to, known standard anions and unusual examples such as halides (F, Cl, Br, I), triflate, tetrafluoroborate, hexafluorophosphate, nitrate, hexafluoroantimonate, any of the numerous mono- or di-anionic carboranes (for the dianionic carboranes X and Y are not separate but the same molecule), tetraphenyl borate and variants thereof (e.g., tetraaryl borates with fluorine substitutions $(F_{1-5})$, trifluoromethyl substitutions $(CF_3)_{1-3}$, other alkyl substitutions $(C_1$-$C_{60})$, and/or aryl substitutions $(Ar_{1-3})$), hydrates thereof, or combinations thereof.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

The following examples relate to forming and testing various unsymmetrical salts and CCC-NHC complexes disclosed herein. The photophysical properties (absorptions, emissions, lifetimes, and quantum yields) of these new platinum complexes were studied. The molecular structures of six (6) salt complexes and eight (8) new platinum complexes were determined by X-ray crystallography, and are provided herein as species examples of the larger genera of the invention. The solid-state photostability data, the radiative lifetime, and quantum yield are also reported. Although unsymmetrical CCC-NHC pincer platinum complexes are generally discussed in the examples, it is to be understood that the disclosure is not so limited and related metal complexes may be used.

Example 1

Synthesis of Azoles, Salts, and Anion Exchange

Mono-hetrocycle azole—an azole (21.2 mmol), 1,3-dibromobenzene (5.00 g, 21.2 mmol), CuO (506 mg, 6.36 mmol), $K_2CO_3$ (4.40 g, 31.8 mmol), and 75 mL of DMSO were combined and heated at 150° C. for 48 hours. The reaction was cooled, a mixture of dichloromethane and isopropanol (150 mL, ratio=10:1) was added, and it was filtered through a pad of basic alumina. The alumina pad was washed with a mixture of dichloromethane and isopropanol (500 mL, ratio=10:1), and the resulting filtrate was concentrated under reduced pressure yielding a solid that was purified by column chromatography on silica gel.

Mono-azolium salt—A 1-(3-bromophenyl)azole (2.77 mmol), an alkyl halide (55.4 mmol), and acetonitrile (5.71 g) were combined and stirred at 120° C. After cooling to room temperature, the volatiles were removed under reduced pressure yielding a white solid.

Unsymmetrical bis(azole)—a bromoarylazole (22.5 mmol), a heterocyclic azole (22.5 mmol), CuO (540 mg, 6.76 mmol), $K_2CO_3$ (7.47 g, 54.1 mmol), and 30 mL of DMSO were combined and heated at 150° C. until all starting material was consumed. The reaction was cooled, a mixture of dichloromethane and isopropanol (250 mL, ratio=10:1) was added, and it was filtered through a pad of basic alumina. The alumina pad was washed with mixture of dichloromethane and isopropanol (500 mL, ratio=10:1), and the resulting filtrate was concentrated under reduced pressure yielding a solid that was purified by column chromatography on silica gel.

Bis(azolium) salt—an unsymmetrical bis(azole) (3.84 mmol), an alkyl halide (38.4 mmol) and acetonitrile (15 mL) were combined and sealed. The reaction was degassed with nitrogen for 3 min and heated at 160° C. The solvent was removed under reduced pressure yielding an oil. The oil was washed with diethyl ether (3×5 mL) and hexanes (3×5 mL) and dried under vacuum yielding a solid.

Mono-aryl, mono-alkyl bis(azolium) salt (Method A)—1-(3-bromophenyl)-4-butyl-1,2,4-triazol-4-ium iodide (0.500 g, 1.23 mmol), imidazole (83.7 mg, 1.23 mmol), CuO (29.4 mg, 0.369 mmol), $K_2CO_3$ (0.487 g, 2.95 mmol), and DMSO (5 mL) were combined in a round bottom flask. The flask was fitted with a condenser and heated for 72 h at 150° C. The reaction mixture was cooled to room temperature, diluted with CH2Cl2 (50 mL) and passed through Celite. The Celite was then washed with $CH_2Cl_2$ (50 mL) and volatiles were removed under reduced pressure. The crude solid (248 mg, 0.627 mmol) was reacted with bis(4-tert-butylphenyl) iodonium triflate (1.02 g, 1.88 mmol), $Cu(OAc)_2.H_2O$ (5.7 mg, 0.0314 mmol) in DMF (5 mL). Crystals grew from the reaction mixture.

Mono-aryl, mono-alkyl bis(azolium) salt (Method B)—An unsymmetrical bis(azole) (0.60 mmol), a bisaryl iodonium triflate (0.60-1.80 mmol), copper acetate hydrate (0.04 mmol), and DMF (9 mL) were heated at 120° C. for 24 h under an inert atmosphere. Upon cooling and concentration, the product was isolated by column chromatography eluting with dichloromethane:acetone (5:1). The mono-arylated product (0.1-0.2 mmol), an alkyl halide (2.0-2.4 mmol), and acetonitrile (0.3-1 mL) were combined under an inert atmosphere and heated at 120° C. for 16 h. After cooling the precipitate was collected by filtration.

Anion exchange—A bis(azolium) halide salt (0.677 mmol) in MeOH (15 mL) was added to sodium tetraphenylborate (2.03 mmol) in MeOH (10 mL). A white precipitate was immediately formed after combining the two solutions. The white precipitate was collected over a filter frit, washed with MeOH (3×5 mL) and diethyl ether (3×5 mL), and dried under vacuum overnight yielding a white solid.

Synthesis of Unsymmetrical Bis(Azolium) Salts

Synthesis of the unsymmetrical bis(azolium) salts began by reacting imidazole (2), 2-methylimidazole (3), 2-phenylimidazole (4), 1,2,4-triazole (5), benzimidazole (6), or 5,6-dimethylbenzimidazole (7) with dibromobenzene (1) to generate mono-azole arenes 8-15 (Scheme 1 shown in FIG. 2). While after 24 h no starting material was present in the synthesis of 8-9 and 11-15, the sterically congested 2-phenylimidazole derivative, 10, required a longer reaction time of 72 h. Monitoring the preparation of 9 via thin layer chromatography (TLC) provided further insight into the rate of conversion. The formation of 1,3-bis(2-methylimidazole) benzene was found to become competitive with the formation of the mono-product 9 after 24 h. This information aided in the acquisition of higher yields of the remaining compounds. All future syntheses of mono(azole) substituted benzenes were worked up before product competition began. There was a clear trend showing the effect of steric congestion at the imidazole C-2 position on yield (8>9>10). A decrease in yield was noted when comparing an unsubstituted imidazole (8) to benzimidazole derivatives (12 and 13). Due to potential biological investigations, the methodology was extended to include examples of 1,2- and 1,4-substituted arenes.

The potential applications for this methodology was extended by the alkylation of several of the mono(azole) benzenes (Scheme 2 shown in FIG. 3). Excellent yields were achieved in the alkylation of 8 or 11 with butyl halides (Cl, Br, and I). It was interesting to note that the iodide salt 16 was obtained as a room temperature ionic liquid.

Figure 4:
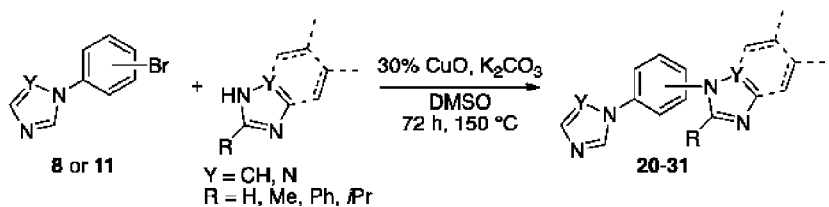
FIG. 4 shows a schematic view of the synthesis of unsymmetrical bis(azole)benzenes according to an embodiment of the disclosure.
Figure 4:
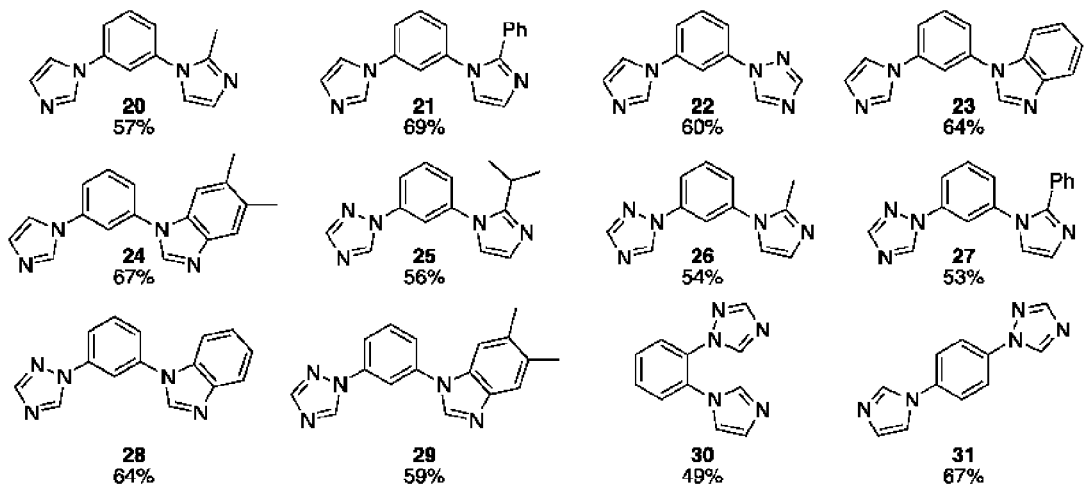

Subsequent reactions for the synthesis of unsymmetrical bis(azole)benzenes were conducted primarily with 8 or 11 with a triazole, benzimidazole, or imidazole (Scheme 3 shown in FIG. 4). All products were obtained in moderate to good yield on a multigram scale. As in the mono(azole) substituted benzene case, there was a similar trend in yield as seen between the substitution patterns (1,4>1,3>1,2). The reaction of 8 and 11 with imidazole derivatives substituted at the C-2 position yielded compounds featuring a potential for mixed NHC/aNHC ligand (20, 21, 25, 26, 27), when bound to a metal. Many of the compounds (22, 25-31) feature a 1,2,4-triazole as one lateral donor group, providing potentially diverse donor properties.

Figure 5:
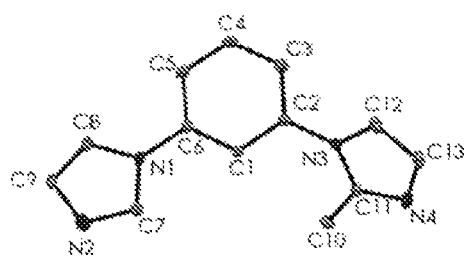
FIG. 5 shows an image illustrating the X-ray molecular structure of 20 according to an embodiment of the disclosure. Hydrogen atoms are omitted for clarity. Thermal ellipsoids are shown at 50% probability.

X-ray quality crystals of compounds 20 were obtained by slow vapor diffusion of $Et_2O$ into a $CH_2Cl_2$ solution. An ORTEP illustration of the molecular structure of compound 20 was shown in FIG. 5. In the absence of a transition metal, the structure is Cl symmetric. The C-2 substituted heterocyclic substituent was twisted out of the plane of the phenylene bridge (20: C1-C2-N3-C11, 56.72(13)° in the opposite direction of the unsubstituted imidazole substituent. This twist was due to the steric bulk of the methyl substituent at C-2. The crystal of 20 was found to be in a chiral space group (P212121) and contains only one enantiomer in the single crystal by spontaneous chiral resolution. Presumably the mixture contains an equal number of the alternate enantiomer.

The final step in the synthesis of these unsymmetrical precursors was the alkylation to give bis(azolium) salts (Scheme 4 shown in FIG. 6). At a 1 g scale, all salts were isolated in high yield. As mentioned before, one compound (21) was reacted with several butyl halides (Cl, Br, I) to give 33-35 with varying halogen counter ions. While all of the halide salts of 21 were isolated in high yield, the iodide salt provided a 95% yield in 16 h whereas the bromide and chloride salts required longer reaction times and higher temperatures. The isolation of the iodide derivative was also much easier than that of the bromide and chloride due to its tendency to precipitate out of the reaction mixture. All iodide salts were isolated as light yellow crystalline solids, which are of sufficient quality for further elaboration. If removal of any remaining iodine was necessary, the solid was dissolved in $CH_2Cl_2$ and washed with a saturated aqueous solution of sodium thiosulfate to obtain a white solid with minimal loss in yield.

Figure 7:
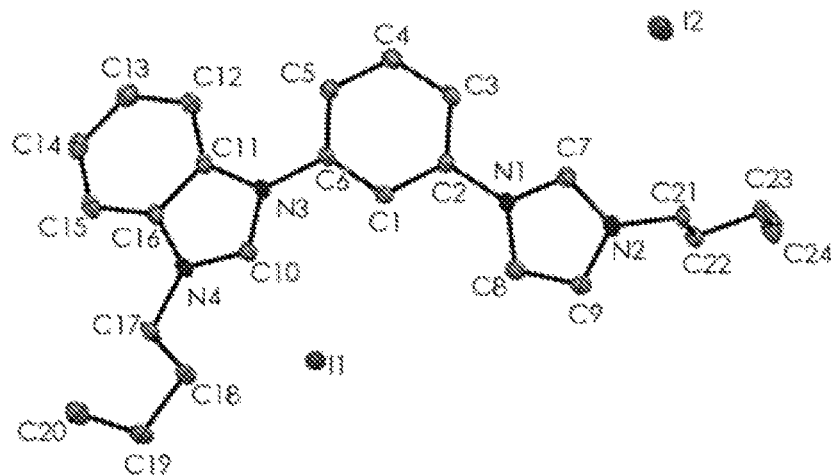
FIG. 7 shows an image illustrating the X-ray molecular structure of 37 according to an embodiment of the disclosure. Hydrogen atoms are omitted for clarity. Thermal ellipsoids are shown at 50% probability.

X-ray quality crystals of compound 37 were obtained by slow vapor diffusion of $Et_2O$ into a $CH_2Cl_2$ solution. The ORTEP diagram in FIG. 7 shows the salt twisted, minimizing the steric interactions between arene and the heterocycles. The benzimidazolium donor group was twisted out of the plane of the phenylene bridge (C1-C6-N3-C10, 40.8 (2)° and in opposite direction from the imidazolium donor group (C1-C2-N1-C8, −33.2(3)°).

Conclusions

The reported methodology efficiently yielded unsymmetrical bis(azolium) salts in only three isolation steps. Furthermore, it has been shown that this methodology was not limited to imidazolium systems, but was applicable to other heterocyclic systems. This method will allow for a modular approach and greater diversity in the design of transition metal ligands, antibacterial agents, ionic liquids, and many other systems exploiting azolium salts.

Example 2

Synthesis and Characterization

Figure 8:
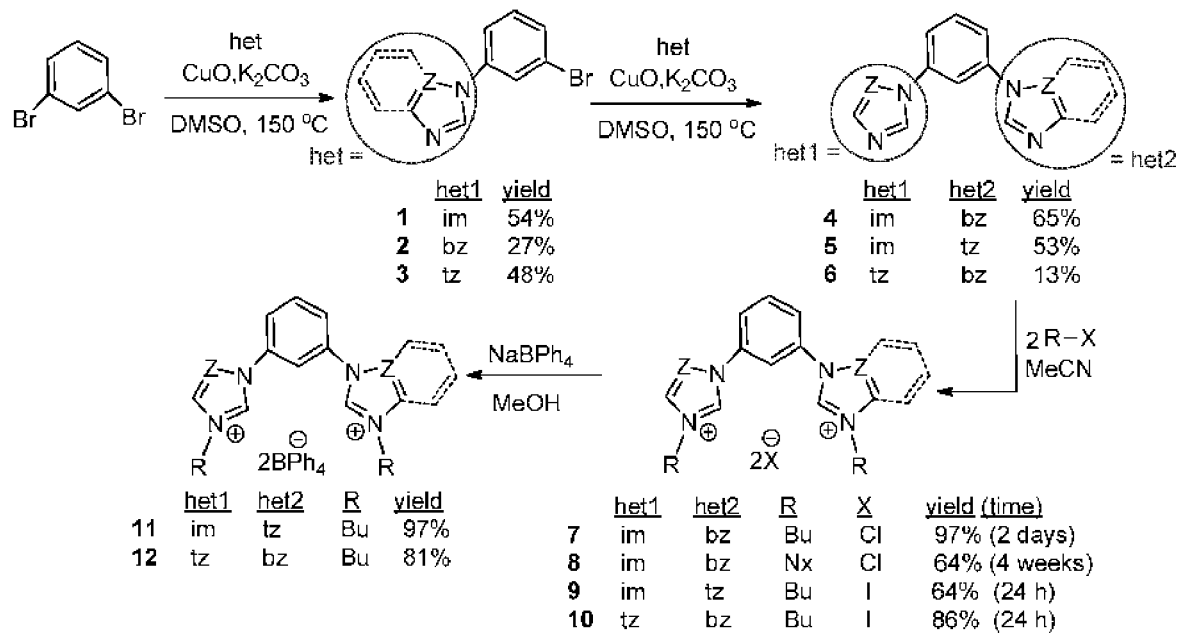
FIG. 8 shows a schematic view of the synthesis of unsymmetrical bis(azolium) salts according to an embodiment of the disclosure. (het=heterocycle; im=imidazole; bz=benzimidazole; tz=1,2,4-triazole).

The adapted methods were used to synthesize ligand 1, 2, and 3. Ligand 4, 5, and 6 and iodide salt 9 and 10 were synthesized following the published procedures. Chloride salts 7 and 8 were synthesized using a similar alkylation method with butyl chloride and neohexyl chloride respectively, as illustrated in FIG. 8. Tetraphenylborate salts (11, 12) were synthesized by reacting the corresponding iodide salt with sodium tetraphenylborate in a methanol solution with high yields (81% and 99%, respectively) (see FIG. 8).

Figure 9:
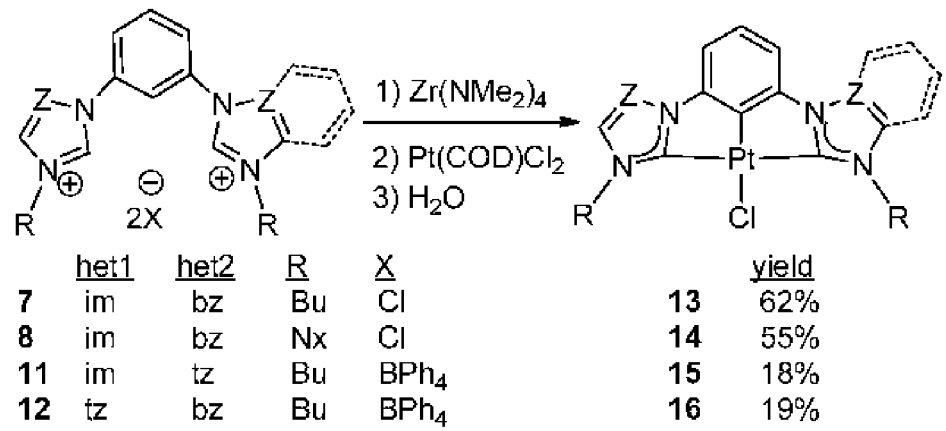
FIG. 9 shows a schematic view of in situ metalation and transmetalation.
Figure 10:
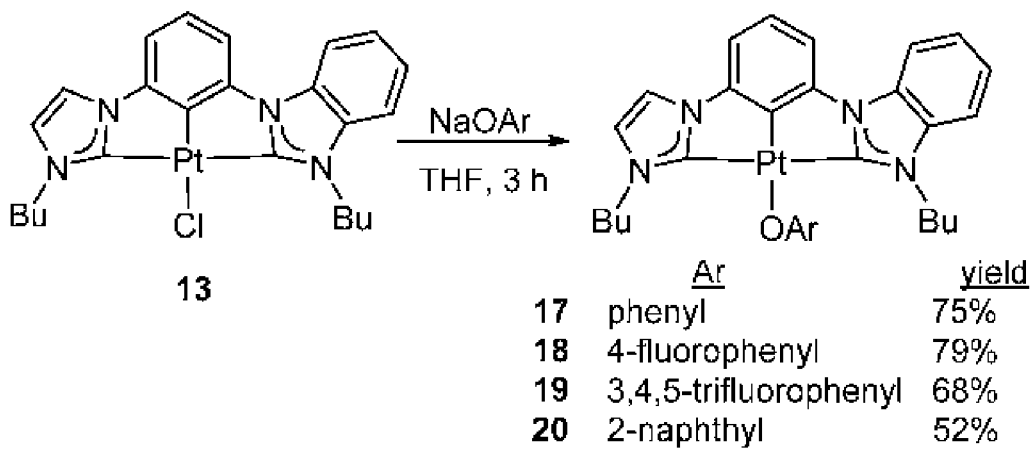
FIG. 10 shows a schematic view of the synthesis of platinum (metal) complexes according to an embodiment of the disclosure.

Unsymmetrical CCC-NHC pincer platinum complexes were for first time synthesized as illustrated in FIG. 9. The synthesis of complexes 13-16 was performed following standard procedures. The platinum bound chloride of complex 13 was substituted with an OAr group as illustrated in FIG. 10.

Mono-Ligated Metal Complexes

The mono-ligated metal complexes of Formula III may be generally described in the alternate form of Formula VI.

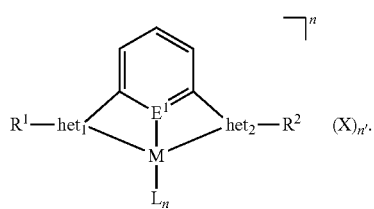

(VI)

M=any transition metal, metal, or metalloid (esp. Rh, Ir, Co, Ni, Pd, Pt, Fe, Ru, Os, Mn, V, Cu).

$E^1$=C or N.

n—represents the charge on the complex and it may be negative or positive and typically in the range of −2 to +3, but may be outside that range.

n'—represents the number of counter-ions (X) necessary to balance the charge n on the pincer complex.

$L_n$=any neutral or charged ligand that may be monodentate, bidentate, or tridentate $het^1$ and $het^2$ are defined as heterocycles based on nitrogen containing one or more nitrogen atoms and may include other heteroatoms. Examples include those based on imidazoles, triazoles, CACCs, imidazolines, pyrazoles, and benzimidazoles including normal and abnormal binding modes. $het^1$ is not equal to $het^2$.

$R^1$, $R^2$=are alkyl or aryl substituents containing from 1-50 carbons and may contain heteroatoms such as N, O, and S. These substituents may be the same or may be different. Various additional substituents may also be present around the rings.

Illustrative Examples of Mono-Ligated Metal Complexes

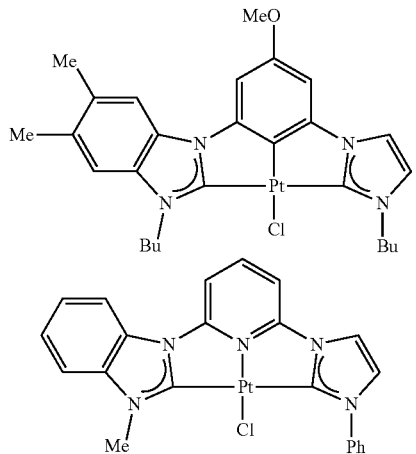

General procedure: Two bis-salts were combined in an organic solvent and treated with zirconium tetrakisdimethyl amido (1-2.5 equivalents) in the temperature range of −78° C. to 160° C. for a period of time between 10 min-2 d. [$PtCl_2$(COD)] (1 equivalent) was then added, and the reaction continued in the same temperature range and/or time period. After quenching the reaction with water, the product may be isolated by column chromatography on silica or alumina.

General Methodology

All chemicals were purchased from Sigma Aldrich, Fisher Scientific, or Strem and were used as received. All solvents used in reactions were taken from dry solvent system or were dried by passing through an oven-dried basic alumina column. All alkylation reactions were carried out under $N_2$ atmosphere. All reactions involving organometallic reagents were carried out in an argon-filled glovebox.

Figure 11:
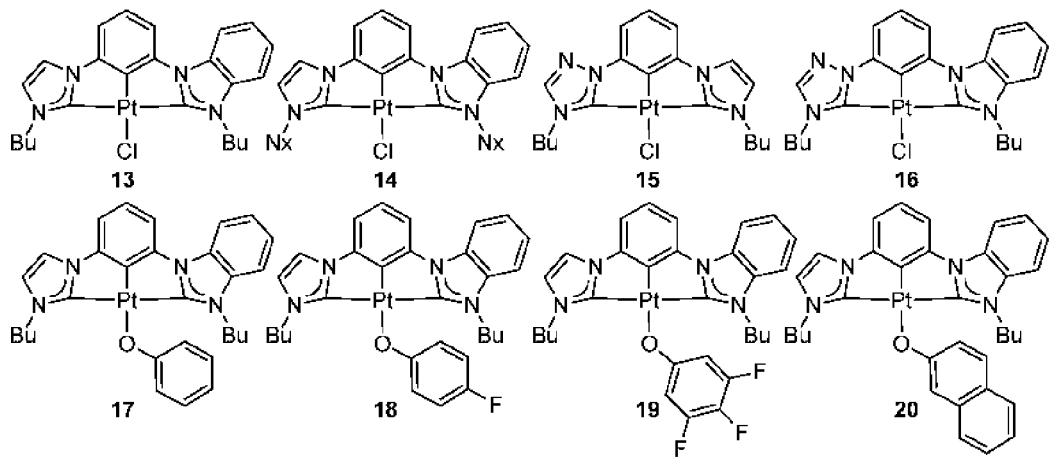
FIG. 11 shows images of various unsymmetrical CCC-NHC platinum complexes according to embodiments of the disclosure. (Bu=butyl; Nx=neohexyl).

The following characterizations are provided for each disclosed complex 1-20. It should be noted that, while platinum is used throughout the metal containing complexes (complexes 13-20, see FIG. 11), other appropriate metals, such as nickel, cobalt, iridium, iron, ruthenium, osmium, vanadium, copper, manganese, rhodium, and palladium may be used in the metal complexes instead of platinum.

1-(3-bromophenyl)-1H-imidazole (1): This complex was adapted from the literature.[1] Imidazole (9.20 g, 135 mmol), 1,3-dibromobenzene (16.4 mL, 135 mmol), CuO (3.22 g, 40.5 mmol), $K_2CO_3$ (44.8 g, 324 mmol), and 175 mL of DMSO were combined and heated at 150° C. for 24 hours. The reaction was cooled, mixture of dichloromethane and isopropanol (300 mL, ratio=10:1) was added, and the reaction mixture was filtered through a column of basic alumina. The alumina pad was washed with mixture of dichloromethane and isopropanol (500 mL, ratio=10:1), and the resulting filtrate was concentrated under reduced pressure yielding an orange oil (16.1 g, 54%) that was purified by column chromatography on silica gel eluting with DCM/IPA (10:1). $^1H$, $^{13}C$ NMR spectra are identical with the data published before. LRMS (ESI): m/z 224.8 ([M+H]$^+$, calculated for $C_9H_8N_2Br$ 224.9).

1-(3-bromophenyl)-1H-benzimidazole (2): This complex was adapted from the literature.[2] Benzimidazole (2.50 g, 21.2 mmol), 1,3-dibromobenzene (5.00 g, 21.2 mmol), CuO (506 mg, 6.36 mmol), $K_2CO_3$ (4.40 g, 31.8 mmol), and 75 mL of DMSO were combined and heated at 150° C. for 48 hours. The reaction was cooled, mixture of dichloromethane and isopropanol (150 mL, ratio=10:1) was added, and the reaction mixture was filtered through a column of basic alumina. The alumina pad was washed with mixture of dichloromethane and isopropanol (500 mL, ratio=10:1), and the resulting filtrate was concentrated under reduced pressure yielding a yellow solid (1.56 g, 27%) that was purified by column chromatography on silica gel eluting with DCM/IPA (10:1). $^1H$, $^{13}C$ NMR spectra are identical with the data published before. LRMS (ESI): m/z 274.7 ([M+M]$^1$, calculated for $C_{13}H_{10}N_2Br$ 274.9).

1-(3-bromophenyl)-1H-triazole (3): This complex was adapted from the literature.[3] Triazole (2.34 g, 33.9 mmol), 1,3-dibromobenzene (8.00 g, 33.9 mmol), CuO (814 mg, 10.2 mmol), $K_2CO_3$ (7.03 g, 50.9 mmol), and 100 mL of DMSO were combined and heated at 150° C. for 24 hours. The reaction was cooled, mixture of dichloromethane and isopropanol (200 mL, ratio=10:1) was added, and the reaction mixture was filtered through a column of basic alumina. The alumina pad was washed with mixture of dichloromethane and isopropanol (500 mL, ratio=10:1), and the resulting filtrate was concentrated under reduced pressure yielding a white solid (3.15 g, 42%) that was purified by column chromatography on silica gel eluting with DCM/IPA (10:1). $^1H$, $^{13}C$ NMR spectra are identical with the data published before. HRMS (ESI) m/z 223.9825 ([M+H]$^+$ calculated for $C_8H_7BrN_3$: 223.9818).

1-(3-(1H-imidazol-1-yl)phenyl)-1H-benzo[d]imidazole (4): 1-(3-bromophenyl)-1H-imidazole (5.0 g, 22.5 mmol), benzimidazole (2.66 g, 22.5 mmol), CuO (540 mg, 6.76 mmol), $K_2CO_3$ (7.47 g, 54.1 mmol), and 30 mL of DMSO were combined and heated at 150° C. for 36 hours. The reaction was cooled, mixture of dichloromethane and isopropanol (250 mL, ratio=10:1) was added, and the reaction mixture was filtered through a column of basic alumina. The alumina pad was washed with mixture of dichloromethane and isopropanol (500 mL, ratio=10:1), and the resulting filtrate was concentrated under reduced pressure yielding a yellow solid (3.80 g, 65%) that was purified by column chromatography on silica gel eluting with DCM/IPA (10:1).

$^1H$ NMR (600.13 MHz, CDCl$_3$): 8.19 (s, 1H), 8.03 (s, 1H), 7.93 (s, 1H), 7.74 (t, 1H, J=7.8 Hz), 7.58 (m, 5H), 7.40 (d, 2H). $^{13}C$ NMR (150.91 MHz, CDCl$_3$): δ140.7, 134.4, 126.9, 125.9, 125.4, 123.7, 123.4, 119.6, 112.9. LRMS (ESI): m/z 260.9 ([M+H]$^+$, calculated for $C_{16}H_{13}N_4$ 261.0).

1-(3-(1H-imidazol-1-yl)phenyl)-1H-1,2,4-triazole (5): 1-(3-bromophenyl)-1H-imidazole (2.0 g, 9.0 mmol), triazole (0.75 g, 10.8 mmol), CuO (0.21 g, 2.7 mmol), $K_2CO_3$ (1.87 g, 13.5 mmol), and 30 mL of DMSO were combined and heated at 150° C. for 5 days. The reaction was cooled, mixture of dichloromethane and isopropanol (150 mL, ratio=10:1) was added, and the reaction mixture was filtered through a column of basic alumina. The alumina pad was washed with mixture of dichloromethane and isopropanol (500 mL, ratio=10:1), and the resulting filtrate was concentrated under reduced pressure yielding a yellow solid (0.81 g, 43%) that was purified by column chromatography on silica gel eluting with DCM/IPA (10:1).

$^1H$ NMR (600.13 MHz, CDCl$_3$): 8.67 (s, 1H), 8.14 (s, 1H), 7.98 (s, 1H), 7.85 (s, 1H), 7.65 (m, 2H), 7.44 (d, 2H, J=7.3 Hz), 7.38 (s, 1H), 7.28 (d, 2H, J=9.5 Hz). $^{13}C$ NMR (150.9 MHz, CDCl$_3$): δ155.6, 143.7, 141.4, 140.9, 134.0, 123.3, 120.7, 115.9. LRMS (ESI): m/z 211.9 ([M+H]$^+$, calculated for $C_{11}H_{10}N_5$ 121.0).

1-(3-(1H-1,2,4-triazol-1-yl)phenyl)-1H-benzo[d]imidazole (6): The procedure was analogous to the preparation of complex 5 by using 1-(3-bromophenyl)-1H-benzimidazole (complex 2) (1.0 g, 3.7 mmol), triazole (0.38 g, 5.5 mmol), CuO (0.087 g, 1.1 mmol), $K_2CO_3$ (0.76 g, 5.5 mmol), and 30 mL of DMSO and purified by column chromatography on silica gel eluting with DCM/IPA (10:1) to yield a light yellow solid (0.1 g, ranging in purity from 13%-59%).

$^1H$ NMR (600.13 MHz, CDCl$_3$): 8.68 (s, 1H), 8.20 (s, 1H), 8.17 (s, 1H), 7.99 (s, 1H), 7.92 (m, 1H), 7.77 (m, 2H), 7.61 (m, 2H), 7.40 (m, 2H). $^{13}C$ NMR (150.9 MHz, CDCl$_3$): δ155.7, 146.9, 144.6, 143.7, 141.1, 140.6, 136.0, 134.2, 126.9, 125.93, 125.88, 123.6, 121.3, 118.3, 112.9. LRMS (ESI): m/z 262.0, 283.8 ([M+H]$^+$, calculated for $C_{15}H_{12}N_5$ 262.1; [M+Na]$^+$, calculated for $C_{15}H_{11}N_5Na$ 284.1).

3-butyl-1-(3-(3-butyl-1H-imidazol-3-ium-1-yl)phenyl)-1H-benzo[d]imidazol-3-ium dichloride (7): 1-(3-(1H-imidazol-1-yl)phenyl)-1H-benzo[d]imidazole (1.00 g, 3.84 mmol), butylchloride (4.0 mL, 38.4 mmol) and MeCN (15 mL) were combined in a storage flask. The mixture was degassed with $N_2$ gas for 3 min and heated at 160° C. in a closed system. After heating for 2 days, the mixture was transferred to a round-bottom flask. Solvent was removed under reduced pressure, yielding a red oil. The red oil was washed with diethyl ether (3×5 mL) and hexanes (3×5 mL) and dried under vacuum overnight, yielding a light brown solid (1.66 g, 97%).

$^1H$ NMR (300.13 MHz, DMSO-d$_6$): 10.86 (s, 1H), 10.46 (s, 1H), 8.63 (s, 1H), 8.59 (s, 1H), 8.27 (d, 1H, J=7.5 Hz), 8.14 (m, 5H), 7.80 (quintet, 2H, J=7.3 Hz), 4.65 (t, 2H, J=7.3 Hz), 4.33 (t, 2H, J=6.9 Hz), 2.05 (quintet, 2H, J=7.8 Hz), 1.92 (quintet, 2H, J=7.3 Hz), 1.40 (m, 4H), 0.96 (q, 6H, J=7.3 Hz). $^{13}C$ NMR (125.74 MHz, DMSO-d$_6$): δ143.6, 136.6, 136.3, 134.8, 132.5, 131.7, 131.1, 128.1, 127.6, 126.3, 124.0, 123.8, 121.7, 119.5, 114.7, 114.4, 49.7, 47.4, 31.6, 30.9, 19.6, 19.3, 13.9, 13.8. HRMS (ESI) m/z=409.1971 ([M−Cl]$^+$ calculated for $C_{24}H_{30}ClN_4$: 409.2154).

3-(3,3-dimethylbutyl)-1-(3-(3-(3,3-dimethylbutyl)-1H-imidazol-3-ium-1-yl)phenyl)-1H-benzo[d]imidazol-3-ium dichloride (8): 1-(3-(1H-imidazol-1-yl)phenyl)-1H-benzo[d]imidazole (600 mg, 2.3 mmol), neohexyl chloride (1.6 mL, 11.5 mmol), sodium iodide (50 mg, 0.33 mmol) and MeCN (1 mL) were combined in a storage flask. The mixture was degassed with $N_2$ gas for 3 min and heated at 210° C. in a closed system. After heating for 4 weeks, the mixture was transferred to a round-bottom flask. Solvent was removed under reduced pressure, yielding a brownish solid. The brownish solid was purified with silica gel chromatography (DCM/MeOH=10:1), yielding an off-white solid (735 mg, 64%).

$^1$H NMR (300.13 MHz, DMSO-$d_6$): 10.97 (s, 1H), 10.49 (s, 1H), 8.58 (d, 2H, J=11.3 Hz), 8.14 (m, 6H), 7.81 (quintet, 2H, J=7.5 Hz), 4.64 (t, 2H, J=8.6 Hz), 4.35 (t, 2H, J=8.5 Hz), 2.03 (t, 2H, J=8.2 Hz), 1.89 (t, 2H, J=8.4 Hz), 1.08 (s, 9H), 1.00 (s, 9H). $^{13}$C NMR (150.92 MHz, DMSO-$d_6$): δ146.2, 139.3, 139.0, 137.5, 135.2, 134.2, 133.7, 130.8, 130.3, 128.9, 126.8, 126.4, 124.3, 122.0, 117.3, 117.1, 49.7, 47.4, 46.0, 44.8, 33.1, 33.0, 32.2, 32.1. HRMS (ESI) m/z=465.2549 ([M−Cl]$^+$ calculated for $C_{28}H_{38}ClN_4$: 465.2780)

4-butyl-1-(3-(3-butyl-1H-imidazol-3-ium-1-yl)phenyl)-1H-1,2,4-triazol-4-ium diiodide (9). 1-(3-(1H-imidazol-1-yl)phenyl)-1H-1,2,4-triazole (0.80 g, 3.79 mmol), butyl iodide (2.16 mL, 18.94 mmol), and MeCN (4 mL) were combined in a storage flask. The mixture was degassed with $N_2$ gas for 3 min and heated at 120° C. in a closed system. After heating for 24 h, off-white solid was precipitated out once the mixture was cooled down to room temperature. The mixture was filtered through a filter frit, yielding an off-white solid (1.45 g, 64%).

$^1$H NMR (300.13 MHz, DMSO-$d^6$): 11.11 (s, 1H), 10.01 (s, 1H), 9.60 (s, 1H), 8.46 (d, 2H, J=2.7 Hz), 8.10 (m, 4H), 4.38 (t, 2H, J=7.4 Hz), 4.30 (t, 2H, J=7.1 Hz), 1.94 (m, 4H), 1.38 (m, 4H), 0.98 (m, 9H). $^{13}$C NMR (150.9 MHz, DMSO-$d^6$): δ148.4, 145.5, 139.1, 139.0, 135.2, 126.8, 126.7, 124.6, 124.4, 117.6. HRMS (ESI) m/z 452.1283 ([M−I]$^+$ calculated for $C_{19}H_{27}IN_5$: 452.1306).

3-butyl-1-(3-(4-butyl-1H-1,2,4-triazol-4-ium-1-yl)phenyl)1H-benzo[d]imidazol-3-ium diiodide (10). 1-(3-(1H-1,2,4-triazol-1-yl)phenyl)-1H-benzo[d]imidazole (0.50 g, 1.91 mmol), butyl iodide (1.1 mL, 9.57 mmol), and MeCN (4 mL) were combined in a storage flask. The mixture was degassed with $N_2$ gas for 3 min and heated at 120° C. in a closed system. After heating for 24 h, yellow solid was precipitated out once the mixture was cooled down to room temperature. The mixture was filtered through a filter frit, yielding a yellow solid (1.03 g, 86%).

$^1$H NMR (300.13 MHz, DMSO-$d^6$): 11.11 (s, 1H), 10.01 (s, 1H), 9.60 (s, 1H), 8.46 (d, 2H, J=2.7 Hz), 8.10 (m, 4H), 4.38 (t, 2H, J=7.4 Hz), 4.30 (t, 2H, J=7.1 Hz), 1.94 (m, 4H), 1.38 (m, 4H), 0.98 (m, 9H). $^{13}$C NMR (150.9 MHz, DMSO-$d^6$): δ148.4, 145.5, 139.1, 139.0, 135.2, 126.8, 126.7, 124.6, 124.4, 117.6. HRMS (ESI) m/z 502.1432 ([M−I]$^+$ calculated for $C_{23}H_{29}N_5$: 502.1462).

4-butyl-1-(3-(3-butyl-1H-imidazol-3-ium-1-yl)phenyl)-1H-1,2,4-triazol-4-ium ditetraphenylborate (11). 4-butyl-1-(3-(3-butyl-1H-imidazol-3-ium-1-yl)phenyl)-1H-1,2,4-triazol-4-ium diiodide (100.0 mg, 0.173 mmol) in MeOH (3 mL) was added into sodium tetraphenylborate (177.3 mg, 0.518 mmol) in MeOH (2 mL). A white precipitate was immediately formed after combining the two solutions. The white precipitate was collected over a filter frit, washed with MeOH (3×5 mL) and diethyl ether (3×5 mL), and dried under vacuum overnight yielding a white solid (162 mg, 97%).

$^1$H NMR (300.13 MHz, DMSO-$d_6$): 10.96 (s, 1H), 9.88 (s, 1H), 9.53 (s, 1H), 8.39 1H), 8.35 (s, 1H), 8.13 (d, 1H, J=7.2 Hz), 8.05 (m, 3H), 7.21 (br s, 16H), 6.95 (t, 16H, J=7.3 Hz), 6.81 (m, 8H), 4.35 (t, 2H, J=7.3 Hz), 4.25 (t, 2H, J=7.3 Hz), 1.92 (m, 4H), 1.38 (m, 4H), 0.96 (q, 6H, J=5.9 Hz). $^{13}$C NMR (125.74 MHz, DMSO-$d_6$): δ164.4, 164.0, 163.6, 163.3, 145.8, 142.7, 136.5, 136.42, 136.40, 136.0, 132.5, 125.82, 125.80, 125.78, 125.76, 124.2, 124.0, 122.0, 121.9, 121.7, 114.9, 49.8, 48.4, 31.6, 31.1, 19.3, 19.3, 13.8. HRMS (ESI) m/z 644.3628 ([M−BPh$_4$]$^+$ calculated for $C_{43}H_{47}BN_5$: 644.3926). Anal. Calculated for $C_{67}H_{67}N_5B_2$ 0.2$H_2O$: C, 83.17; H, 7.02; N, 7.24. Found: C, 83.08; H, 7.22; N, 7.30.

3-butyl-1-(3-(4-butyl-1H-1,2,4-triazol-4-ium-1-yl)phenyl)1H-benzo[d]imidazol-3-ium ditetraphenylborate (12). 3-butyl-1-(3-(4-butyl-1H-1,2,4-triazol-4-ium-1-yl)phenyl)-1H-benzo[d]imidazol-3-ium diiodide (200 mg, 0.318 mmol) in MeOH (6 mL) was added into sodium tetraphenylborate (326 mg, 0.953 mmol) in MeOH (4 mL). A white precipitate was immediately formed after combining the two solutions. The white precipitate was collected over a filter frit, washed with MeOH (3×5 mL) and diethyl ether (3×5 mL), and dried under vacuum overnight yielding a white solid (260 mg, 81%).

$^1$H NMR (300.13 MHz, DMSO-$d_6$): 11.05 (s, 1H), 10.26 (s, 1H), 9.53 (s, 1H), 8.47 (s, 1H), 8.23 (d, 2H, J=7.9 Hz), 8.09 (d, 2H, J=4.5 Hz), 7.91 (d, 1H, J=8.1 Hz), 7.78 (m, 2H), 7.21 (br s, 16H), 6.95 (t, 16H, J=7.3 Hz), 6.81 (m, 8H), 4.60 (t, 2H, J=7.1 Hz), 4.36 (t, 2H, J=7.3 Hz), 1.97 (m, 4H), 1.43 (m, 4H), 0.96 (m, 6H). $^{13}$C NMR (125.74 MHz, DMSO-$d_6$): δ164.4, 164.1, 164.0, 163.9, 163.7, 163.3, 145.8, 143.3, 142.9, 136.6, 136.0, 134.8, 132.7, 131.7, 131.5, 128.1, 127.7, 125.81, 125.79, 125.77, 125.75, 122.8, 122.0, 118.4, 114.7, 113.9, 48.4, 47.4, 31.1, 30.0, 19.6, 19.3, 13.9, 13.8. HRMS (ESI) m/z 694.3809 ([M−BPh$_4$]$^+$ calculated for $C_{47}H_{49}BN_5$: 694.4083). Anal. Calculated for $C_{71}H_{69}N_5B_2$0.9$H_2O$: C, 82.78; H, 6.93; N, 6.80. Found: C, 82.78; H, 6.80; N, 6.87.

2-(1-N-((butyl)imidazol-2-ylidene)-3-N-((butyl)benzimidazo-2-ylidene)phenylene) chloroplatinum(II) (13). In a nitrogen-filled glovebox, 3-(3,3-dimethylbutyl)-1-(3-(3-(3,3-dimethylbutyl)-1H-imidazol-3-ium-1-yl)phenyl)-1H-benzo[d]imidazol-3-ium dichloride (100 mg, 0.225 mmol) was added to Zr(NMe$_2$)$_4$ (90 mg, 0.337 mmol) in 4 mL of dry toluene in an oven dried vial with a magnetic stir bar. The mixture was stirred for 3 hours at 120° C. to afford a dark red homogenous solution. Then Pt(COD)Cl$_2$ (82 mg, 0.225 mmol) and 6 mL of DCM was added to mixture, and the solution was stirred overnight at room temperature. Water (0.5 mL) was added to mixture after it was taken out from glovebox. The mixture was filtered through Celite. The volatiles were removed under reduced pressure. The resulting orange solid was washed with acetone (3×1 mL) and dried under reduced pressure to yield a yellow solid (84.2 mg, 62%).

$^1$H NMR (500.13 MHz, CDCl$_3$): 8.00 (d, 1H, J=8.0 Hz), 7.53 (d, 1H, J=8.0 Hz), 7.47 (t, 1H, J=7.3 Hz), 7.40 (m, 3H), 7.25 (t, 2H, J=8.0 Hz), 7.00 (d, 2H, J=2.0 Hz), 6.95 (q, 1H, J=8.0 Hz), 5.09 (t, 2H, J=7.3 Hz), 4.79 (t, 2H, J=7.3 Hz), 2.00 (quintet, 2H, J=7.6 Hz), 1.93 (quintet, 2H, J=7.6 Hz), 1.60 (sextet, 2H, J=7.6 Hz), 1.50 (sextet, 2H, J=7.6 Hz), 1.00 (t, 6H, J=7.6 Hz). $^{13}$C NMR (125.74 MHz, CDCl$_3$): δ 181.3 ($^1$J(Pt−C)=1178.6 Hz), 173.5 ($^1$J(Pt−C)=1156.8 Hz), 145.7 (J=11.3 Hz), 144.6 (J=11.3 Hz), 134.9 (J=13.5 Hz), 134.6, 131.5 (J=22.5 Hz), 124.4, 123.6, 123.3, 120.7 (J=12.9 Hz), 114.9 (J=20.2 Hz), 111.7, 111.3, 109.0 (J=16.5 Hz), 107.2 (J=16.5 Hz), 49.3, 46.4, 33.8, 32.6, 20.1, 19.8, 14.0, 13.9. $^{195}$Pt NMR (107.08 MHz, CDCl$_3$): −4076 ppm. HRMS (ESI) m/z 566.1799 ([M−Cl]$^+$ calculated for C$_{24}$H$_{27}$N$_4$Pt: 566.1880). Anal. Calculated for C$_{24}$H$_{27}$N$_4$PtCl 0:056CH$_2$Cl$_2$: C, 47.62; H, 4.50; N, 9.23. Found: C, 47.49; H, 4.57; N, 9.16.

2-(1-N-((neohexyl)imidazol-2-ylidene)-3-N-((neohexyl) benzimidazo-2-ylidene) phenylene)chloroplatinum(II) (14). The procedure was analogous to the preparation of complex 13 by using 3-butyl-1-(3-(3-butyl-1H-imidazol-3-ium-1-yl) phenyl)-1H-benzo[d] imidazol-3-ium dichloride (100 mg, 0.20 mmol), Zr(NMe$_2$)$_4$ (80 mg, 0.30 mmol), 4 mL of toluene, Pt(COD)Cl$_2$ (74 mg, 0.20 mmol), 6 mL of DCM and 0.5 mL of water to yield a light yellow solid (71.6 mg, 55%).

$^1$H NMR (500.13 MHz, CDCl$_3$): 8.02 (d, 1H, J=7.5 Hz), 7.46 (m, 2H), 7.39 (m, 3H), 7.25 (m, 1H), 5.13 (m, 2H), 4.85 (m, 2H), 1.90 (m, 4H), 1.17 (s, 9H), 1.00 (s, 9H). $^{13}$C NMR (125.74 MHz, CDCl$_3$): δ181.1, 173.6, 145.8, 144.6, 134.9, 134.7, 131.6, 124.4, 123.5, 123.3, 120.3, 115.1, 111.6, 111.3, 108.9, 107.1, 46.3, 45.3, 43.6, 43.4, 30.3, 30.2, 29.7, 29.6. $^{195}$Pt NMR (107.08 MHz, CDCl$_3$): −4069 ppm. HRMS (ESI) m/z 622.2464 ([M−Cl]$^+$ calculated for C$_{28}$H$_{35}$N$_4$Pt: 622.2506). Anal. Calculated for C$_{28}$H$_{35}$N$_4$PtCl0.052HNMe$_2$: C, 51.11; H, 5.40; N, 8.59. Found: C, 50.83; H, 5.79; N, 8.37.

2-(1-N-((butyl)triazol-2-ylidene)-3-N-((butyl)imidazo-2-ylidene)phenylene)chloroplatinum (II) (15): In a nitrogen-filled glovebox, 3-butyl-1-(3-(4-butyl-1H-1,2,4-triazol-4-ium-1-yl)phenyl)-1H-benzo[d]imidazol-3-ium ditetraphenylborate (20 mg, 0.0207 mmol) was added to Zr(NMe$_2$)$_4$ (9.4 mg, 0.0352 mmol) in 1 mL of DCM in an oven dried vial with a magnetic stir bar. The mixture was stirred at 45° C. for 16 h to afford a dark red homogenous solution. Then Pt(COD)Cl$_2$ (7.7 mg, 0.0207 mmol) was added to mixture, and the solution was stirred overnight at room temperature. Water (0.5 mL) was added to mixture after it was taken out from glovebox. The mixture was filtered through Celite. The volatiles were removed under reduced pressure. The resulting yellow-orange solid was purified with column chromatography on silica gel eluting with DCM. A light yellow solid (2 mg, 18%) was yielded after removing solvent under reduced pressure.

$^1$H NMR (300.13 MHz, CDCl$_3$): 8.04 (s, 1H), 7.41 (s, 1H), 7.22 (m, 2H), 7.00 (m, 2H), 4.71 (m, 4H), 1.94 (m, 4H), 1.49 (sextet, 4H, J=7.7 Hz), 1.28 (q, 6H, J=4.7 Hz). $^{13}$C NMR (150.9 MHz, CDCl$_3$): δ178.6 (t, J=1151.4 Hz), 175.0 (t, J=1217.6 Hz), 147.4, 146.4, 144.3 (t, J=14.7 Hz), 135.1, 126.4, 123.3 (t, J=14.4 Hz), 117.7 (t, J=22.7 Hz), 111.6 (t, J=17.4 Hz), 110.9 (t, J=16.4 Hz), 52.1, 50.2, 36.4, 36.1, 22.4, 22.3, 16.5, 16.3. $^{195}$Pt NMR (107.08 MHz, CDCl$_3$): −4158 ppm. HRMS (ESI) m/z 517.1532 ([M−Cl]$^+$ calculated for C$_{19}$H$_{24}$N$_5$PtCl: 517.1675).

2-(1-N-((butyl)triazol-2-ylidene)-3-N-((butyl)benzimidazo-2-ylidene)phenylene) chloroplatinum(II) (16): The procedure was analogous to the preparation of complex 13 by using 3-butyl-1-(3-(4-butyl-1H-1,2,4-triazol-4-ium-1-yl)phenyl)-1H-benzo[d]imidazol-3-ium ditetraphenylborate (20 mg, 0.0197 mmol), Zr(NMe$_2$)$_4$ (8.9 mg, 0.0335 mmol), 4 mL of DCM, Pt(COD)Cl$_2$ (7.4 mg, 0.0197 mmol), and 0.5 mL of water to result a yellow-orange solid. Light yellow solid (2.2 mg, 19%) was yielded after purifying with column chromatography on silica gel eluting with DCM.

$^1$H NMR (300.13 MHz, CDCl$_3$): 8.07 (s, 1H), 8.03 (d, 1H, J=7.9 Hz), 7.52 (m, 4H), 7.28 (m, 2H), 5.07 (t, 2H, J=7.6 Hz), 4.78 (t, 2H, J=7.3 Hz), 2.00 (m, 4H), 1.57 (m, 4H), 1.05 (q, 6H, J=6.9 Hz). $^{13}$C NMR (150.9 MHz, CDCl$_3$): 183.0 (t, J=1234.2 Hz), 179.0 (t, J=1130.3 Hz), 148.3 (t, J=9.3 Hz), 146.2, 144.4 (t, J=14.9 Hz), 137.6 (t, J=15.4 Hz), 135.1, 134.1 (t, J=22.4 Hz), 127.4, 126.7, 126.2, 114.6, 114.1, 112.5 (t, J=16.2 Hz), 111.4 (t, J=17.1 Hz), 50.2, 49.3, 36.1, 35.3, 22.8, 22.4, 16.7, 16.4. $^{195}$Pt NMR (107.08 MHz, CDCl$_3$): −4116 ppm. HRMS (ESI) m/z 567.1713 ([M−Cl]$^+$ calculated for C$_{23}$H$_{26}$N$_5$PtCl: 567.1832).

2-(1-N-((butyl)imidazol-2-ylidene)-3-N-((butyl)benzimidazo-2-ylidene)phenylene) (phenoxyl) platinum(II) (17). 2-(1-N-((butyl)imidazol-2-ylidene)-3-N-((butyl)benzimidazo-2-ylidene)phenylene) chloroplatinum(II) (complex 13) (20.0 mg, 54.3 μmol, sodium phenoxide (5.7 mg, 81.4 μmol, and THF (1 mL) were combined in a screw-capped vial in argon-filled glovebox. Reaction was ultra-sounded for 3 hours. The reaction mixture was then filtered through Celite. The solvent was removed, and the residual was dissolved in THF (0.5 mL) and hexanes (2 mL) was added slowly. Yellow crystals were formed after siting in glovebox overnight and collected (16.3 mg, 75%).

$^1$H NMR (300.13 MHz, acetone-d$_6$): 8.20 (d, 1H, J=8.1 Hz), 7.88 (m, 1H), 7.74 (d, 1H, J=7.9 Hz), 7.51 (m, 3H), 7.38 (m, 1H), 7.21 (quintet, 2H, J=5.9 Hz), 6.88 (m, 4H), 6.28 (t, 1H, J=6.7 Hz), 4.65 (t, 2H, J=7.9 Hz), 4.19 (t, 2H, J=7.9 Hz), 1.67 (m, 4H), 1.10 (m, 4H), 0.73 (m, 9H). $^{13}$C NMR (150.9 MHz, acetone-d$_6$): δ211.7, 185.9, 178.5, 174.2, 148.9, 148.2, 137.1, 136.7, 134.6, 131.8, 130.9, 127.3, 126.1, 125.9, 123.4, 122.0, 118.8, 114.8, 114.6, 114.0, 111.6, 110.2, 71.0, 51.2, 48.6, 36.4, 35.3, 22.4, 22.0, 16.0, 15.9. $^{195}$Pt NMR (107.08 MHz, acetone-d$_6$): −3931 ppm. $^{195}$Pt NMR (107.08 MHz, CDCl$_3$): −3931 ppm. HRMS (ESI) m/z 566.1824 ([M−OPh]$^+$ calculated for C$_{24}$H$_{27}$N$_4$Pt: 566.1880).

2-(1-N-((butyl)imidazol-2-ylidene)-3-N-((butyl)benzimidazo-2-ylidene)phenylene)(4-fluorophenolate) platinum(II) (18). The procedure was analogous to the preparation of complex 17 by using 2-(1-N-((butyl)imidazol-2-ylidene)-3-N-((butyl)benzimidazo-2-ylidene)phenylene) chloroplatinum(II) (13) (30.0 mg, 54.3 μmol), sodium 4-fluorophenolate (9.4 mg, 81.4 μmol), and THF (1 mL) to yield a yellow solid (8.3 mg, 85%).

$^1$H NMR (CDCl$_3$, 500.13 MHz): HRMS (ESI) m/z 566.1805 ([M−C$_6$H$_4$FO]$^+$ calculated for C$_{24}$H$_{27}$N$_4$Pt: 566.1880).

2-(1-N-((butyl)imidazol-2-ylidene)-3-N-((butyl)benzimidazo-2-ylidene)phenylene)(3,4,5-trifluorophenolate) platinum(II) (19). The procedure was analogous to the preparation of complex 17 by using 2-(1-N-((butypimidazol-2-ylidene)-3-N-((butyl)benzimidazo-2-ylidene)phenylene) chloroplatinum(II) (complex 13) (30.0 mg, 54.3 μmol), sodium 3,4,5-trifluorophenolate (9.4 mg, 81.4 μmol), and THF (1 mL) to yield a yellow solid (8.3 mg, 85%).

$^1$H NMR (CDCl$_3$, 500.13 MHz): HRMS (ESI) m/z 566.1771 ([M−C$_6$H$_2$F$_3$O]$^+$ calculated for C$_{24}$H$_{27}$N$_4$Pt: 566.1880).

2-(1-N-((butyl)imidazol-2-ylidene)-3-N-((butyl)benzimidazo-2-ylidene)phenylene)([1,1'-biphenyl]-4-olate) platinum(II) (20). The procedure was analogous to the preparation of complex 17 by using 2-(1-N-((butyl)imidazol-2-ylidene)-3-N-((butyl)benzimidazo-2-ylidene)phenylene) chloroplatinum(II) (complex 13) (30.0 mg, 54.3 [mol), sodium naphthalen-2-olate (9.4 mg, 81.4 μmol), and THF (1 mL) to yield a yellow solid (8.3 mg, 85%).

$^1$H NMR (CDCl$_3$, 500.13 MHz): HRMS (ESI) m/z 566.1792 ([M−C$_1$H$_7$O]$^+$ calculated for C$_{24}$H$_{27}$N$_4$Pt: 566.1880).

Example 3

Bis-Ligated Metal Complexes

The bis-ligated metal complexes of Formula IV may be generally described in the alternate form of Formula VII.

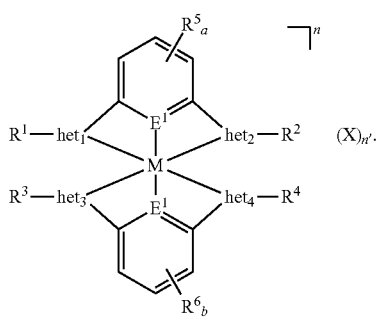

(VII)

M=any transition metal, metal, or metalloid (esp. Rh, Ir, Co, Ni, Pd, Pt, Fe, Ru, Os, Mn, V, Cu).

$E^1$, $E^2$=C or N and $E^1$ may be equal to $E^2$ or $E^1$ may not be equal to $E^2$ n represents the charge on the complex and it may be negative or positive and typically in the range of −2 to +3, but may be outside that range.

n' represents the number of counterions (X) necessary to balance the charge n on the pincer complex.

$R^1$, $R^2$, $R^3$, $R^4$=are alkyl or aryl substituents containing from 1-50 carbons and may contain heteroatoms such as N, O, and S. These substituents may all be the same, may all be different, or any combination in between.

$het^1$, $het^2$, $het^3$, and $het^4$ are defined as heterocycles based on nitrogen containing one or more nitrogen atoms and may include other heteroatoms. They may all be the same or different or any combination in between. Examples include those based on imidazoles, triazoles, CACCs, imidazolines, pyrazoles and benzimidazoles including normal and abnormal binding modes. When $het^1$ is not equal to $het^2$, $het^3$ may equal $het^4$. Various additional substituents may also be present around the rings as illustrated for $R^5$ and $R^6$ with the number of substituents a or b equal to 1-3. The substituents may be the same or different.

Illustrative Examples of Bis-Ligated Metal Complexes

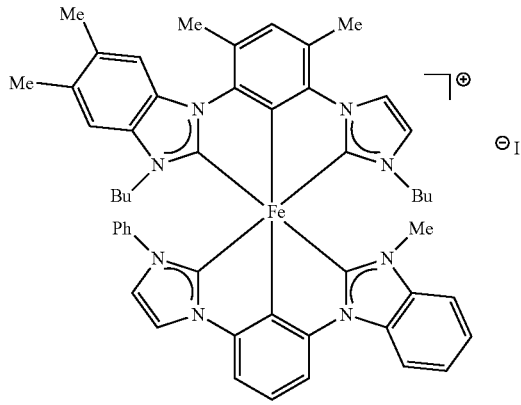

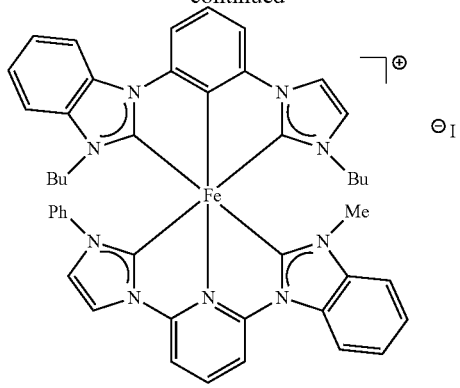

General procedure: Two bis-salts were combined in an organic solvent and treated with zirconium tetrakisdimethyl amido (1-2.5 equivalents) in the temperature range of −78° C. to 160° C. for a period of time between 10 min-2 d. $FeCl_3$ (1 equivalent) was then added, and the reaction continued in the same temperature range and/or time period. A mixture of products is obtained after quenching the reaction with water. The products may be separated by column chromatography on silica or alumina.

General Methodology

All chemicals were purchased from Sigma Aldrich, Fisher Scientific, or Strem and were used as received. All solvents used in reactions were taken from dry solvent system or were dried by passing through an oven-dried basic alumina column. All alkylation reactions were carried out under $N_2$ atmosphere. All reactions involving organometallic reagents were carried out in an argon-filled glovebox.

The following characterizations are provided for various symmetrical and unsymmetrical bis-ligated complexes. It should be noted that, while platinum is used throughout the metal containing complexes, other appropriate metals, such as nickel, cobalt, iridium, iron, ruthenium, osmium, vanadium, copper, manganese, rhodium, and palladium may be used in the metal complexes instead of platinum.

Symmetrical

Bis(1,3-bis(N-butyl-imidazol-2'-ylidene)phenylene)iron (III) Iodide (Route 1) 1,3-bis(1-butyllimidizol-3-yl)benzene diiodide (0.1154 g, 0.20 mmol) and $Zr(NMe_2)_4$ (0.0724 g, 0.27 mmol) were combined in THF (15 mL) under an inert atmosphere and stirred for 2 hours. $FeCl_3$ (0.046 g, 0.28 mmol) was added and stirred overnight. Water (40 μL, 2.2 mmol) was added, producing a precipitate that was removed and washed with MeCN (3×5 mL) and concentrated and dried under vacuum. The product was isolated via silica column chromatography. DCM to was used remove impurities, then MeCN to collect a dark blue band which was concentrated giving the product as a dark blue glassy solid (0.0504 g, 61.2%).

Bis(1,3-bis(N-butyl-imidazol-2'-ylidene)phenylene)iron (III) Iodide (Route 2) 1,3-bis(1-butyllimidizol-3-yl)benzene diiodide (0.117 g, 0.205 mmol) and $Zr(NMe_2)_4$ (0.0861 g, 0.322 mmol) were combined in THF (15 mL) under an inert atmosphere and stirred for 2 hours. $FeCl_2$ (34.1 g, 0.210 mmol) was added and stirred overnight. Water (40 μL, 2.2 mmol) was added, producing a precipitate that was removed and washed with MeCN (3×5 mL) and concentrated and dried under vacuum. The product was isolated via silica column chromatography. DCM to was used remove impurities, then MeCN to collect a dark blue band which was concentrated giving the product as a dark blue glassy solid (0.0687 g, 81.1%).

$^1$H NMR (CD$_2$Cl$_2$, 500 MHz): δ24.66 (s, 4H), 9.21 (s, 8H), 1.90 (s, 12H), 0.95 (s, 12H), −0.98 (s, 8H), −2.55 (s, 4H), −36.52 (s, 2H). ESI-MS (m/z): observed, 698.3486 for [M−I]$^+$; calcd, 698.3508 for (C$_{40}$H$_{50}$N$_8$Fe).

Bis(1,3-bis(N-methyl-imidazol-2'-ylidene)phenylene) iron(III) Iodide 1,3-bis(1-methylimidizol-3-yl)benzene diiodide (0.1066 g, 0.22 mmol) and Zr(NMe$_2$)$_4$ (0.0958 g, 0.36 mmol) were combined in THF (15 mL) under inert atmosphere and stirred for 2 hours. FeCl$_3$ (0.0521 g, 0.32 mmol) was added and stirred overnight. Water (40 μL, 2.2 mmol) was added, producing a precipitate that was removed and washed with MeCN (3×5 mL) and concentrated and dried under vacuum. The product was isolated via silica column chromatography. DCM to was used remove impurities, then MeCN to collect a dark blue band which was concentrated giving the product as a dark blue glassy solid (0.0189 g, 26.6%).

$^1$H NMR (CD$_2$Cl$_2$, 500 MHz): δ24.85 (s, 4H), 9.73 (s, 12H) 2.56 (s, 4H), −2.83 (s, 4H), −36.68 (s, 2H). ESI-MS (m/z): observed, 530.1537 for [M−1]$^+$; calcd, 530.1630 for (C$_{28}$H$_{26}$N$_8$Fe).

Bis(1,3-bis(N-benzylimidazol-2'-ylidene)phenylene)iron (III) Bromide 1,3-bis(1-benzylimidizol-3-yl)benzene dibromide (0.1223 g., 0.22 mmol) and Zr(NMe2)$_4$ (0.0907 g, 0.33 mmol) were combined in THF (15 mL) under inert atmosphere and stirred for 2 hours. FeCl$_3$ (0.0359 g, 0.22 mmol) was added and stirred overnight. Water (40 μL, 2.2 mmol) was added, producing a precipitate that was removed and washed with THF (3×5 mL) and concentrated and dried under vacuum. The product was isolated via silica column chromatography. DCM to was used remove impurities, then MeCN to collect a dark blue band which was concentrated giving the product as a dark blue glassy solid (0.0113 g, 14.0%).

$^1$H NMR (CD$_2$Cl$_2$, 500 MHz): δ25.24 (s, 4H), 10.92 (s, 8H), 6.65 (t, 4H, J=7.3 Hz), 6.36 (t, 8H, J=7 Hz), 3.92 (d, 8H, J=7.4 Hz), 2.18 (s, 4H), −3.00 (s, 4H), −35.83 (s, 2H). ESI-MS (m/z): observed, 834.2774 for [M−I]$^+$; calcd, 834.2882 for (C$_{52}$H$_{42}$N$_8$Fe).

Bis(1,3-bis-(N-butyl-benzimidazol-2'-ylidene)phenylene) iron(III) Iodide (Route 1) 1,3-bis(1-butyllbenzimidizol-3-yl) benzene diiodide (0.2977 g, 0.44 mmol) and Zr(NMe$_2$)$_4$ (0.1891 g, 0.71 mmol) were combined in THF (40 mL) under inert atmosphere and stirred for 2 hours. FeCl$_3$ (0.071 g, 0.44 mmol) was added and stirred overnight. Water (40 μL, 2.2 mmol) was added, producing a precipitate that was removed and washed with THF (3×15 mL) and concentrated and dried under vacuum. The product was isolated via silica column chromatography. DCM to was used remove impurities, then MeCN to collect a dark blue band which was concentrated giving the product as a dark blue glassy solid (0.130 g, 57.2%).

Bis(1,3-bis(N-butyl-benzimidazol-2'-ylidene)phenylene) iron(III) Iodide (Route 2) 1,3-bis(1-butyllbenzimidizol-3-yl) benzene (0.1072 g, 0.157 mmol) and Zr(NMe$_2$)$_4$ (0.0678 g, 0.253 mmol) were combined in THF (15 mL) under an inert atmosphere and stirred for 2 hours. FeCl$_2$ (0.0343 g, 0.272 mmol) was added and stirred overnight. Water (40 μL, 2.2 mmol) was added, producing a precipitate that was removed and washed with MeCN (3×5 mL) and concentrated and dried under vacuum. The product was isolated via silica column chromatography. DCM to was used remove impurities, then MeCN to collect a dark blue band which was concentrated giving the product as a dark blue glassy solid (0.0649 g, 80.6%).

$^1$H NMR (CD$_2$Cl$_2$, 500 MHz): δ30.03 (s, 4H), 10.71 (s, 4H), 10.38 (s, 8H), 7.43 (s, 4H), 5.47 (s, 4H), 4.43 (s, 4H), 2.98 (s, 8H), 1.08 (s, 12H), −1.92 (s, 8H), −42.93 (s, 2H). ESI-MS (m/z): observed, 798.3807 for [M−I]$^+$; calcd, 798.3821 for (C$_{48}$H$_{54}$N$_8$Fe).

Bis(1,3-bis(N-butyl-triazol-2'-ylidene)phenylene)iron (III) Iodide 1,3-bis(1-butylltriazol-3-yl)benzene diiodide (0.102 g, 0.176 mmol) and Zr(NMe$_2$)$_4$ (0.0799 g, 0.299 mmol) were combined in THF (15 mL) under inert atmosphere and stirred for 2 hours. FeCl$_3$ (32.2 g, 0.198 mmol) was added and stirred overnight. Water (40 μL, 2.2 mmol) was added, producing a precipitate that was removed and washed with THF (3×15 mL) and concentrated and dried under vacuum. The product was isolated via silica column chromatography. DCM to was used remove impurities, then MeCN to collect a dark blue band which was concentrated giving the product as a dark blue glassy solid (0.0051 g, 6.8%).

$^1$H NMR (CD$_2$Cl$_2$, 500 MHz): δ24.72 (s, 4H), 9.27 (s, 8H), 1.94 (s, 8H), 1.00 (s, 12H), −0.93 (s, 8H), −2.51 (s, 4H), 34.29 (s, 2H).

Bis(1,3-bis(N-butyl-imidazol-2'-ylidene)phenylene)iron (III) Tetraphenylborate (Route 1) 1,3-bis(1-benzylimidizol-3-yl)benzene di-tetraphenylborate (0.0999 g, 0.10 mmol) and Zr(NMe$_2$)$_4$ (0.0752 g, 0.28 mmol) were combined in THF (15 mL) under inert atmosphere and stirred for 1 hour. FeCl$_3$ (0.0243 g, 0.15 mmol) was added and stirred overnight. Water (40 μL mL, 2.2 mmol) was added, producing a precipitate that was removed and washed with THF (3×5 mL) and concentrated and dried under vacuum. The product was isolated via silica column chromatography. DCM to was used to remove impurities and MeCN was used to collect a dark blue band which was concentrated giving the product as a dark blue glassy solid (0.0334 g, 63%).

Bis(1,3-bis(N-butyl-imidazol-2'-ylidene)phenylene)iron (III) Tetraphenylborate (Route 2) 1,3-bis(1-benzylimidizol-3-yl)benzene di-tetraphenylborate (0.0102 g, 0.104 mmol) and Zr(NMe$_2$)$_4$ (0.0464 g, 0.174 mmol) were combined in THF (15 mL) under an inert atmosphere and stirred for 2 hours. FeCl$_2$ (0.0181 g, 0.111 mmol) was added and stirred overnight. Water (40 μL, 2.2 mmol) was added, producing a precipitate that was removed and washed with MeCN (3×5 mL) and concentrated and dried under vacuum. The product was isolated via silica column chromatography. DCM to was used remove impurities, then MeCN to collect a dark blue band which was concentrated giving the product as a dark blue glassy solid (0.0444 g, 83%).

Bis(1,3-bis(N-butyl-imidazol-2'-ylidene)phenylene)iron (III) Tetraphenylborate (Route 3) Bis-[2-(1,3-Bis(N-butyl-imidazol-2-ylidene)phenylene)] iron(III) iodide (0.011 g, 0.013 mmol) was dissolved in 1 mL of MeOH, sodium tetraphenylborate (0.008 g, 0.025 mmol) was dissolved in a separate 1 mL portion of MeOH. The two were combined and left for 24 hrs, after which time the product crystalized out as purple crystals (0.005 g, 37%).

$^1$H NMR (CDlC$_3$, 300 MHz): δ24.39 (s, 4H), 9.11 (s, 8H), 7.03 (s, 8H), 6.63 (m, 12H), 1.95 (s, 8H), 1.64 (s, 4H), 0.98 (t, 12H, J=6.3 Hz), −1.01 (s, 8H), −2.87 (s, 4H), −34.40 (s, 2H).

Bis(1,3-bis(N-butyl-benzimidazol-2'-ylidene)phenylene) iron(Ill) Tetraphenylborate Bis(1,3-bis(N-butyl-benzimidazol-2'-ylidene)phenylene)iron(III) iodide (0.013 g, 0.012 mmol) was dissolved in 1 mL of MeOH, sodium tetraphenylborate (0.013 g, 0.041 mmol) was dissolved in a separate 1 mL portion of MeOH. The two were combined and left for 24 hrs, after which time the product crystallized out as purple crystals, these were filtered and washed with hexanes. (0.0082 g, 54%).

$^1$H NMR (CD$_2$Cl$_2$, 500 MHz): δ29.99 (s, 4H), 10.69 (d, 4H, J=8.3 Hz), 10.38 (s, 8H), 7.43 (d, 4H, J=7.2 Hz), 7.34 (s, 8H), 7.02 (t, 8H, J=7.2 Hz), 6.84 (t, 4H, J=7.0 Hz), 5.46 (t, 4H, J=7.3 Hz), 4.40 (d, 4H, J=7.8 Hz), 2.98 (s, 8H), 1.08 (s, 12H), −1.92 (s, 8H), −42.90 (s, 2H)

Bis-[2-(1,3-Bis(N-butyl-imidazol-2-ylidene)phenylene)] iron(II) Bis-[2-(1,3-Bis(N-butyl-imidazol-2-ylidene)phenylene)] iron(III) iodide (0.011 g, 0.013 mmol) and cobaltocene (0.04 g, 0.021 mmol) were combined in MeCN (1 mL) and left for 15 minutes. The product crystallized out, which were filtered and washed with MeCN (3×0.2 mL). as orange crystals which were suitable for Xray analysis (0.0068 g, 78%).

$^1$H NMR (CD$_2$Cl$_2$, 300 MHz): δ7.40 (d, 4H, J=7.2 Hz), 7.36 (s, 4H), 6.45 (s, 6H), 2.63 (t, 8H, J=7.7 Hz), 0.61 (s, 20H), 0.48 (m, 8H)

Bis-[2-(1,3-Bis(N-benzylimidazol-2-ylidene)phenylene)] iron(II) Bis-[2-(1,3-Bis(N-benzyl-imidazol-2-ylidene)phenylene)] iron(III) iodide (0.0084 g, 0.012 mmol) and cobaltocene (0.0021 g, 0.012 mmol) were combined in DCM (1 mL) and left for 5 minutes. The solution was concentrated dissolved in MeCN (0.5 mL) filtered and the solid was washed with MeCN (3×0.2 mL) leaving the product as an orange solid (0.0042 g, 60%).

$^1$H NMR (CD$_2$Cl$_2$, 300 MHz): δ7.26 (s, 4H), 7.00 (d, 8H, J=7.3 Hz), 6.93 (t, 8H, J=7.1 Hz), 6.79 (t, 2H, J=7.5 Hz), 6.40 (s, 4H), 6.24 (d, 8H, J=7.3 Hz), 3.90 (s, 8H).

Bis-[2-(1,3-Bis-(N-butylbenzimidazol-2-ylidene)phenylene)] iron(II) Bis-[2-(1,3-Bis(N-butylbenz-imidazol-2-ylidene)phenylene)] iron(III) iodide (0.0197 g, 0.02 mmol) and cobaltocene (0.0071 g, 0.03 mmol) were combined in MeCN (1 mL) and left for 15 minutes. The product precipitated out as a yellow solid (0.0091 g, 52%).

$^1$H NMR (CD$_2$Cl$_2$, 300 MHz): δ8.01 (d, 4H, J=7.8 Hz), 7.81 (d, 4H, J=7.8 Hz), 7.43 (t, 2H, J=6.4 Hz), 7.14 (t, 4H, J=7.8 Hz), 6.98 (d, 4H, J=8.0 Hz), 6.81 (d, 4H, J=7.8 Hz), 2.92 (s, 8H), 0.67 (s, 8H), 0.46 (t, 20H, J=3 Hz)

Bis(1,3-bis(N-butyl-benzimidazol-2'-ylidene)5-nitrophenylene)iron(III) hydrogen dinitrate Bis(1,3-bis(N-butyl-benzimidazol-2'-ylidene)phenylene)iron(III) Iodide was dissolved in DCM and excess H$_2$SO$_4$ (1M in Et$_2$O) was added and stirred for a few minutes before excess HNO$_3$ was added and the solution was left to stir for an hour. The organic layer was washed with water (3×) to extract any excess acid and concentrated, azeotroping off any excess water with toluene, giving a brown solid.

Unsymmetrical Bis[2-[1-(N-butylbenzimidazol-2-ylidene)-3-(N-butyl-imidazol-2-ylidene)phenylen]iron(III) Iodide 1-(N-butylbenzimidazol-2-ylidene)-3-(N-butylimidazol-2-ylidene) benzene diiodide (0.0964 g, 0.15 mmol) and Zr(NMe$_2$)$_4$ (0.069 g, 0.26 mmol) were combined in THF (15 mL) under inert atmosphere and stirred for 2 hours. FeCl$_3$ (0.027 g, 0.17 mmol) was added and stirred for 18 hrs. Water (40 µL, 2.2 mmol) was added, producing a precipitate that was removed and washed with THF (3×5 mL) and MeCN (3×5 mL). The product was isolated via silica column chromatography. DCM to was used remove impurities, then MeCN to collect a blue band which was concentrated giving the product as a blue glassy solid (0.0303 g, 42.7%). ESI-MS (m/z): observed, 898.4155 for [M−I]$^+$; calcd, 898.4134 for (C$_{56}$H$_{58}$N$_8$Fe)

Bis[2-[1-(N-butylbenzimidazol-2-ylidene)-3-(N-butyl-imidazol-2-ylidene)phenylene]iron(II) Bis[2-[1-(N-butyl-benzimidazol-2-ylidene)-3-(N-butylimidazol-2-ylidene) phenylene]iron(III) (0.01 g, 0.011 mmol) and cobaltocene (0.0032 g, 0.017 mmol) were combined in MeCN (1 mL) and left for 15 minutes. The product crystalized out as orange crystals (0.0075 g, 87%).

$^1$H NMR (CD$_2$Cl$_{26}$, 500 MHz): δ7.95 (d, 2H, J=7.8 Hz), 7.72 (d, 2H, J=7.0 Hz), 7.55 (s, 2H), 7.25 (m, 4H), 7.11 (t, 2H, J=7.1 Hz), 6.97 (t, 2H, J=7.7 Hz), 6.79 (d, 2H, J=7.6 Hz), 6.55 (s, 2H), 2.92 (t, 4H, J=7.9 Hz), 2.57 (t, 4H, J=7.2 Hz), 0.64 (s, 8H), 0.52 (m, 20H).

Bis[2-[1-(N-butylbenzimidazol-2-ylidene)-3-(N-butyltriazol-2-ylidene)phenylene]iron(III) Tetraphenyl borate 1-(N-butylbenzimidazol-2-ylidene)-3-(N-butyltriazol-2-ylidene) benzene ditetraphenylborate (0.1073 g, 0.11 mmol) and Zr(NMe$_2$)$_4$ (0.086 g, 0.32 mmol) were combined in THF (15 mL) under inert atmosphere and stirred for 2 hours. FeCl$_3$ (0.0195 g, 0.12 mmol) was added and stirred for 18 hrs. Water (40 µL, 2.2 mmol) was added, producing a precipitate that was removed and washed with THF (3×5 mL). The product was isolated via silica column chromatography. DCM to was used remove impurities, then MeCN to collect a blue band which was concentrated giving the product as a blue glassy solid (0.0034 g, 5.7%).

Example 4

Illustrative Examples of Unsymmetrical Bimetallics

Substituents around the rings, as shown for the may be included but are not explicitly illustrated below

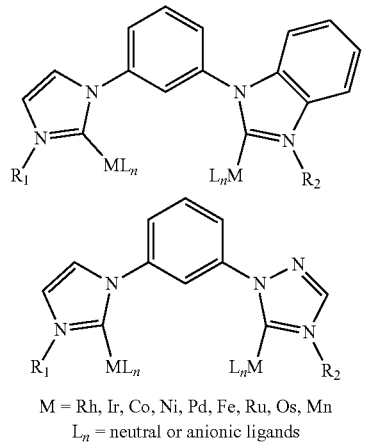

M = Rh, Ir, Co, Ni, Pd, Fe, Ru, Os, Mn
L$_n$ = neutral or anionic ligands

The heterocycles may be 1,3-substituted around the aryl ring as illustrated, and are also conceived as 1,2-substituted or 1,4-substituted around the aryl ring. The metals, M, may be the same, and may be different.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Dua, R.; Shrivastava, S.; Sonwane, S. K.; Srivastava, S. K. Adv. Bio. Res. 2011, 5, 120.

2. D'Anna, F.; Nimal Gunaratne, H. Q.; Lazzara, G.; Noto, R.; Rizzo, C.; Seddon, K. R. Org. Biomol. Chem. 2013, 11, 5836.
3. Hillesheim, P. C.; Singh, J. A.; Mahurin, S. M.; Fulvio, P. F.; Oyola, Y.; Zhu, X.; Jiang, D.-c.; Dai, S. RSC Adv. 2013, 3, 3981.
4. Malhotra, S. V.; Kumar, V.; Velez, C.; Zayas, B. MedChemComm 2014, 5, 1404.
5. Martinez-Guerrero, L. J.; Wright, S. H. J. Pharmacol. Exp. Ther. 2013, 346, 495.
6. Meyer, D.; Strassner, T. J. Org. Chem. 2010, 76, 305.
7. Zheng, D.; Dong, L.; Huang, W.; Wu, X.; Nie, N. Renew. Sustainable Energy Rev. 2014, 37, 47.
8. Teyssot, M.-L.; Jarrousse, A.-S.; Manin, M.; Chevry, A.; Roche, S.; Norre, F.; Beaudoin, C.; Morel, L.; Boyer, D.; Mahiou, R.; Gautier, A. Dalton Trans. 2009, 6894.
9. Luo, Y.; Lu, Y.-H.; Gan, L.-L.; Zhou, C.-H.; Wu, J.; Geng, R.-X.; Zhang, Y.-Y. Arch. Pharm. Chem. Life Sci. 2009, 342, 386.
10. Demberelnyamba, D.; Kim, K.-S.; Choi, S.; Park, S.-Y.; Lee, H.; Kim, C.-J.; Yoo, I.-D. Bioorg. Med. Chem. Lett. 2004, 12, 853.
11. Hindi, K. M.; Panzner, M. J.; Tessier, C. A.; Cannon, C. L.; Youngs, W. J. Chem. Rev. 2009, 109, 3859.
12. Pernak, J.; Sobaszkiewicz, K.; Mirska, I. Green Chem. 2003, 5, 52.
13. Crandall, I. E.; Zhao, B.; Vlahakis, J. Z.; Szarek, W. A. Bioorg. Med. Chem. Lett. 2013, 23, 1522.
14. Gao, Y. V., J. Z.; Szarek, W. A.; Brockhausen, I. Bioorg. Med. Chem. 2013, 21, 1305.
15. Yoon, J.; Kim, S. K.; Singh, N. J.; Kim, K. S. Chem. Soc. Rev. 2006, 35, 355.
16. Sajoto, T.; Djurovich, P. I.; Tamayo, A.; Yousufuddin, M.; Bau, R.; Thompson, M. E.; Holmes, R. J.; Forrest, S. R. Inorg. Chem. 2005, 44, 7992.
17. Son, S. U.; Park, K. H.; Lee, Y.-S.; Kim, B. Y.; Choi, C. H.; Lah, M. S.; Jang, Y. H.; Jang, D.-J.; Chung, Y. K. Inorg. Chem. 2004, 43, 6896.
18. Unger, Y.; Zeller, A.; Ahrens, S.; Strassner, T. Chem. Comm. 2008, 3263.
19. Chianese, A. R.; Li, X.; Janzen, M. C.; Faller, J. W.; Crabtree, R. H. Organometallics 2003, 22, 1663.
20. Danopoulos, A. A.; Pugh, D.; Smith, H.; SaBmannshausen, J. Chem. Eur. J. 2009, 15, 5491.
21. Diez-Gonzalez, S.; Marion, N.; Nolan, S. P. Chem. Rev. 2009, 109, 3612.
22. Kantchev, E. A. B.; O'Brien, C. J.; Organ, M. G. Angew. Chem., Int. Ed. 2007, 46, 2768.
23. Peris, E.; Crabtree, R. H. Coord. Chem. Rev. 2004, 248, 2239.
24. Bourissou, D.; Guerret, O.; Gabbai, F. P.; Bertrand, G. Chem. Rev. 2000, 100, 39.
25. Aldeco-Perez, E.; Rosenthal, A. J.; Donnadieu, B.; Parameswaran, P.; Frenking, G.; Bertrand, G. Science 2009, 326, 556.
26. Arduengo, A. J.; Harlow, R. L.; Kline, M. J. Am. Chem. Soc. 1991, 113, 361.
27. Bertrand, G. Carbene Chemistry: From Fleeting Intermediates to Powerful Reagents; Taylor & Francis, 2002.
28. Bourissou, D.; Guerret, O.; Gabbai, F. P.; Bertrand, G. Chem. Rev. 2000, 100, 39.
29. Vignolle, J.; Cattoen, X.; Bourissou, D. Chem. Rev. 2009, 109, 3333.
30. Schuster, O.; Yang, L.; Raubenheimer, H. G.; Albrecht, M. Chem. Rev. 2009, 109, 3445.
31. Mizuhata, Y.; Sasamori, T.; Tokitoh, N. Chem. Rev. 2009, 109, 3479.
32. Zuo, W.; Braunstein, P. Dalton Trans. 2012, 41, 636.
33. Clark, W. D.; Tyson, G. E.; Hollis, T. K.; Valle, H. U.; Valente, E. J.; Oliver, A. G.; Dukes, M. P. Dalton Trans. 2013, 42, 7338.
34. Vargas, V. C.; Rubio, R. J.; Hollis, T. K.; Salcido, M. E. Org. Lett. 2003, 4847.
35. Boswell, M. G.; Yeung, F. G.; Wolf, C. Synlett 2012, 23, 1240.
36. Diness, F.; Fairlie, D. P. Angewandte Chemie 2012, 51, 8012.
37. Bettati, M.; Blurton, P.; Carling, W. R.; Chambers, M. S.; Hallett, D. J.; Jennings, A.; Lewis, R. T.; Russell, M. G. N.; Street, L. J.; Szekeres, H. J.; WO 2002038568 A1 (2002).

It will be understood that various details of the presently disclosed subject matter can be changed without departing from the scope of the subject matter disclosed herein. Furthermore, the foregoing description is for the purpose of illustration only, and not for the purpose of limitation.

What is claimed is:
1. An unsymmetrical CCC-NHC metal complex comprising a mono-ligated metal complex according to Formula III:

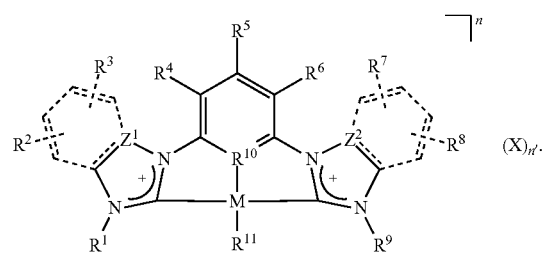

wherein M is selected from the group consisting of Rh, Ir, Co, Ni, Pd, Pt, Fe, Ru, Os, Mn, V, and Cu;
wherein n is the charge on the complex;
wherein each $R^1$-$R^9$ is independently selected from the group consisting of hydrogen, alkyl, aryl, and combinations thereof;
wherein $R^{10}$ is C or N;
wherein $R^{11}$ is a neutral or charged ligand;
wherein X is a counterion and n' is the number of counterions;
wherein $Z^1$ and $Z^2$ are each independently selected from the group consisting of CH, $CR^{12}$, N, and combinations thereof; and
wherein, when $Z^1$ or $Z^2$ is $CR^{12}$, $R^{12}$ includes a substituted or unsubstituted $C_4$ alkyl forming a ring structure with the carbon in the Z position and the azole carbon attached thereto.

2. The unsymmetrical CCC-NHC metal complex of claim 1, wherein M is Pt.

3. The unsymmetrical CCC-NHC metal complex of claim 1, wherein the alkyl is selected from the group consisting of $C_1$-$C_{60}$ alkyl, branched, ethereal, fluorinated, in-line aryl, and combinations thereof.

4. The unsymmetrical CCC-NHC metal complex of claim 1, wherein the aryl is an unsubstituted aryl.

5. The unsymmetrical CCC-NHC metal complex of claim 1, wherein the aryl is a substituted aryl selected from the group consisting of 4-trimethylmethylaryl, an alkyl substituted aryl, a fluorinated aryl, an ethereal substituted aryl, and combinations thereof.

6. The unsymmetrical CCC-NHC metal complex of claim 1, wherein $Z^1$ and $Z^2$ are the same and at least one of $R^1$ differs from $R^9$, $R^2$ differs from $R^8$, $R^3$ differs from $R^7$, or $R^{11}$ differs from $R^{10}$.

7. The unsymmetrical CCC-NHC metal complex of claim 1, wherein $Z^1$ and $Z^2$ are different.

8. A method of forming the unsymmetrical CCC-NHC metal complex of claim 1, the method comprising:
   reacting a dihalogenated benzene with a first azole to form a mono(azole)benzene;
   reacting the mono(azole)benzene with a second azole to form an unsymmetrical bis(azole)benzene;
   alkylating the unsymmetrical bis(azole)benzene to form an unsymmetrical bis(azolium) salt; and
   metalating the unsymmetrical bis(azolium) salt to form the unsymmetrical CCC-NHC metal complex.

\* \* \* \* \*